US012564236B2

(12) United States Patent
Law

(10) Patent No.: US 12,564,236 B2
(45) Date of Patent: *Mar. 3, 2026

(54) POSITIONING AND STABILISING STRUCTURE AND SYSTEM INCORPORATING SAME

(71) Applicant: ResMed Pty Ltd, Bella Vista (AU)

(72) Inventor: Ian Andrew Law, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/959,852

(22) Filed: Nov. 26, 2024

(65) Prior Publication Data

US 2025/0082060 A1     Mar. 13, 2025

Related U.S. Application Data

(63) Continuation of application No. 17/915,033, filed as application No. PCT/AU2020/051081 on Oct. 8, (Continued)

(30) Foreign Application Priority Data

Mar. 27, 2020    (AU) ................................ 2020900953

(51) Int. Cl.
*A42B 3/08*        (2006.01)
*A42B 3/14*        (2006.01)

(52) U.S. Cl.
CPC .............. *A42B 3/085* (2013.01); *A42B 3/145* (2013.01); *A61M 2210/06* (2013.01)

(58) Field of Classification Search
CPC ..... G02B 27/0176; A42B 3/145; A42B 3/085; A61M 2210/06
See application file for complete search history.

(56) References Cited

U.S. PATENT DOCUMENTS 4,913,135 A     4/1990  Mattingly
5,671,037 A     9/1997  Ogasawara et al.
(Continued)

FOREIGN PATENT DOCUMENTS

CN          201826192 U      5/2011
CN          104880823 A      9/2015
(Continued)

OTHER PUBLICATIONS

Notice of Reasons for Refusal mailed Apr. 8, 2025 in Japanese Application No. 2024-043844, with English translation, 6 pages.
(Continued)

*Primary Examiner* — Muhammad N Edun
(74) *Attorney, Agent, or Firm* — Nixon & Vanderhye P.C.

(57)            ABSTRACT
A head-mounted display system includes a head-mounted display unit and a positioning and stabilising structure structured and arranged to hold the head-mounted display unit in an operational position over a user's face in use. The positioning and stabilising structure includes a rear support structure adapted to contact posterior regions of a user's head and at least one connector structured and arranged to interconnect the rear support structure to the head-mounted display unit. The rear support structure is in the form of a hoop comprising an occipital portion configured and arranged engage the user's head along a portion of the occipital bone adjacent a junction where the neck muscles attach to the occipital bone in use.

14 Claims, 16 Drawing Sheets

Related U.S. Application Data 2020, now Pat. No. 12,178,276, which is a continuation-in-part of application No. 16/865,480, filed on May 4, 2020, now Pat. No. 11,243,405, and a continuation-in-part of application No. 16/865,526, filed on May 4, 2020, now Pat. No. 11,262,589.

(56) References Cited

U.S. PATENT DOCUMENTS

| | | | |
|---|---|---|---|
| 5,793,835 | A | 8/1998 | Blanck |
| 5,832,926 | A | 11/1998 | Towlen |
| 7,120,939 | B1 | 10/2006 | Howard et al. |
| 7,390,286 | B1 | 6/2008 | Edgeton |
| 8,553,910 | B1 | 10/2013 | Dong |
| 9,703,103 | B2 | 7/2017 | Araki et al. |
| 9,901,132 | B2 | 2/2018 | Hairston |
| 9,989,998 | B1 | 6/2018 | Yee |
| 10,078,349 | B1 | 9/2018 | Morris |
| 10,130,785 | B2 | 11/2018 | Dravitzki |
| 10,133,305 | B1 | 11/2018 | Sullivan et al. |
| 10,209,738 | B1 | 2/2019 | Tompkins |
| 10,470,512 | B1 | 11/2019 | Yee |
| 10,496,130 | B1 | 12/2019 | Yee |
| 10,739,600 | B1 | 8/2020 | Yee |
| 10,761,567 | B2 | 9/2020 | Ellis et al. |
| 10,860,100 | B2 | 12/2020 | Osterhout et al. |
| 11,169,384 | B2 | 11/2021 | Law |
| 11,243,405 | B2 | 2/2022 | Law |
| 11,262,589 | B2 | 3/2022 | Law |
| 11,565,068 | B2 | 1/2023 | Wells |
| 11,574,472 | B2 | 2/2023 | Herzberg |
| 11,583,447 | B2 | 2/2023 | Woermann |
| 11,598,967 | B2 | 3/2023 | Law |
| 11,619,821 | B2 | 4/2023 | Araki |
| 11,686,948 | B2 | 6/2023 | Law |
| 2003/0115662 | A1 | 6/2003 | Dobbie et al. |
| 2004/0058780 | A1 | 3/2004 | Edgeton |
| 2004/0097839 | A1 | 5/2004 | Epley |
| 2006/0118117 | A1 | 6/2006 | Berthon-Jones |
| 2008/0027400 | A1 | 1/2008 | Harding |
| 2014/0026890 | A1 | 1/2014 | Haskard |
| 2014/0296060 | A1 | 10/2014 | Chen |
| 2016/0044981 | A1 | 2/2016 | Frank et al. |
| 2016/0054570 | A1 | 2/2016 | Bosveld et al. |
| 2016/0082214 | A1 | 3/2016 | Barlow |
| 2016/0140887 | A1 | 5/2016 | Kim |
| 2016/0216512 | A1 | 7/2016 | Miller et al. |
| 2016/0261300 | A1 | 9/2016 | Fei et al. |
| 2017/0017085 | A1 | 1/2017 | Araki |
| 2017/0168303 | A1 | 6/2017 | Petrov |
| 2017/0242262 | A1 | 8/2017 | Fuchs et al. |
| 2017/0261656 | A1 | 9/2017 | Kim et al. |
| 2017/0337737 | A1 | 11/2017 | Edwards et al. |
| 2017/0367423 | A1 | 12/2017 | Reitz et al. |
| 2018/0055202 | A1 | 3/2018 | Miller et al. |
| 2018/0095497 | A1 | 4/2018 | Hsu et al. |
| 2018/0095498 | A1 | 4/2018 | Raffle et al. |
| 2018/0239430 | A1 | 8/2018 | Tadi |
| 2018/0307282 | A1 | 10/2018 | Allin et al. |
| 2018/0335632 | A1 | 11/2018 | Cho et al. |
| 2018/0338130 | A1 | 11/2018 | Miller et al. |
| 2018/0364491 | A1 | 12/2018 | Park et al. |
| 2019/0141847 | A1 | 5/2019 | Chang et al. |
| 2019/0243145 | A1 | 8/2019 | Ellis et al. |
| 2019/0243414 | A1 | 8/2019 | Bae et al. |
| 2019/0258061 | A1 | 8/2019 | Solomon |
| 2019/0258065 | A1 | 8/2019 | Yun et al. |
| 2019/0333480 | A1 | 10/2019 | Lang |
| 2019/0339736 | A1 | 11/2019 | Chang |
| 2020/0033601 | A1 | 1/2020 | Magrath et al. |
| 2020/0042035 | A1 | 2/2020 | Chen et al. |
| 2020/0089007 | A1 | 3/2020 | Maric |
| 2020/0159040 | A1 | 5/2020 | Kiritz |
| 2020/0233453 | A1 | 7/2020 | Hatfield |
| 2021/0041706 | A1 | 2/2021 | Hatfield et al. |
| 2021/0080996 | A1 | 3/2021 | Hudman |
| 2021/0121272 | A1 | 4/2021 | Gad |
| 2021/0263323 | A1 | 8/2021 | Ellis |
| 2021/0302748 | A1 | 9/2021 | Law |
| 2021/0302749 | A1 | 9/2021 | Law |
| 2021/0302750 | A1 | 9/2021 | Law |
| 2022/0026724 | A1 | 1/2022 | Law et al. |
| 2022/0091425 | A1 | 3/2022 | Law |
| 2023/0157400 | A1 | 5/2023 | Law |

FOREIGN PATENT DOCUMENTS

| | | | |
|---|---|---|---|
| CN | 105148374 | A | 12/2015 |
| CN | 205809421 | U | 12/2016 |
| CN | 205958850 | U | 2/2017 |
| CN | 106842577 | A | 6/2017 |
| CN | 208141050 | U | 11/2018 |
| CN | 109085698 | A | 12/2018 |
| CN | 109212761 | A | 1/2019 |
| CN | 109387944 | A | 2/2019 |
| CN | 110190911 | A | 8/2019 |
| CN | 110262039 | A | 9/2019 |
| CN | 209417425 | U | 9/2019 |
| CN | 110308558 | A | 10/2019 |
| CN | 110609387 | A | 12/2019 |
| CN | 110692007 | A | 1/2020 |
| EP | 3 287 865 | A2 | 2/2018 |
| JP | 7-191611 | A | 7/1995 |
| JP | 2002-262196 | A | 9/2002 |
| JP | 4010909 | B2 | 11/2007 |
| JP | 2008-252319 | A | 10/2008 |
| JP | 2012-511341 | A | 5/2012 |
| JP | 2012-186660 | A | 9/2012 |
| JP | 2014-142654 | A | 8/2014 |
| JP | 2014-533185 | A | 12/2014 |
| JP | 2014-534030 | A | 12/2014 |
| JP | 2015-522381 | A | 8/2015 |
| JP | 2016-503699 | A | 2/2016 |
| JP | 2019-129484 | A | 8/2019 |
| JP | 2019-532341 | A | 11/2019 |
| KR | 10-2014-0066258 | | 5/2014 |
| KR | 10-2015-0060698 | A | 6/2015 |
| KR | 10-2017-0037355 | | 4/2017 |
| KR | 10-2018-0136222 | | 12/2018 |
| KR | 10-2019-0117776 | A | 10/2019 |
| KR | 10-2020-0003930 | A | 1/2020 |
| TW | 201400867 | A | 1/2014 |
| TW | 201831956 | A | 9/2018 |
| WO | WO 2009/118552 | A1 | 10/2009 |
| WO | WO 2011/070198 | A1 | 6/2011 |
| WO | WO 2013/049248 | A2 | 4/2013 |
| WO | WO 2018/053509 | A1 | 3/2018 |
| WO | WO 2018/067421 | A1 | 4/2018 |
| WO | WO 2019/190448 | A1 | 10/2019 |
| WO | WO 2019/212591 | A1 | 11/2019 |
| WO | WO 2021/041871 | A1 | 3/2021 |
| WO | WO 2021/189096 | A1 | 9/2021 |

OTHER PUBLICATIONS

First Office Action mailed May 6, 2025 in Chinese Application No. 202010861697.7, with English translation, 22 pages.

Second Office Action mailed Apr. 17, 2025 in Chinese Application No. 202080100252.5, with English translation, 13 pages.

Notification of Transmittal of the International Search Report and the Written Opinion of the International Search Authority mailed Feb. 4, 2021 in International Application No. PCT/AU2020/051081, 7 pages.

Written Opinion of the International Searching Authority mailed Feb. 4, 2021 in International Application No. PCT/AU2020/051081, 8 pages.

Law, U.S. Appl. No. 17/915,033, filed Sep. 27, 2022, for "Positioning and Stabilising Structure and System Incorporating Same," (parent application).

Substantive Examination Adverse Report (Section 30(1)) with Search Report mailed Jan. 31, 2023 in Malaysian Application No. PI2022005337, 3 pages.

(56) References Cited

OTHER PUBLICATIONS

Office Action mailed Mar. 20, 2023 in Japanese Application No. 2022-558257, with English Translation, 6 pages.

Notice of Allowance mailed Sep. 20, 2023 in U.S. Appl. No. 18/100,676, 13 pages.

Taiwanese Office Action mailed Mar. 22, 2024 in Taiwanese Application No. 112117902, with English machine translation, 7 pages.

Notice of Allowance mailed Jan. 25, 2024 in U.S. Appl. No. 18/133,711, 9 pages.

Extended European Search Report mailed Jul. 11, 2023 in European Application No. 20927540.3, 7 pages.

Notice Requesting Submission of Opinion mailed Sep. 3, 2024 in Korean Application No. 10-2023-7024644, with English translation, 28 pages.

Notice of the First Office Action mailed Sep. 28, 2024 in Chinese Application No. 202080100252.5, with English translation, 16 pages.

Decision of Rejection mailed Aug. 26, 2025 in Chinese Application No. 202080100252.5, with English translation, 19 pages.

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Copyright 2020 ResMed

POSITIONING AND STABILISING STRUCTURE AND SYSTEM INCORPORATING SAME

CROSS-REFERENCE TO RELATED APPLICATIONS

This application is a continuation of U.S. application Ser. No. 17/915,033, filed Sep. 27, 2022, which is the U.S. national phase of International Application No. PCT/AU2020/051081 filed Oct. 8, 2020 which designated the U.S. and claims the benefit of Australian Provisional Application No. 2020900953, filed Mar. 27, 2020, each of which is incorporated herein by reference in its entirety. This application is also a continuation-in-part of U.S. application Ser. No. 16/865,480, filed May 4, 2020, and is a continuation-in-part of U.S. application Ser. No. 16/865,526, filed May 4, 2020, each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

FIELD OF THE TECHNOLOGY

The present technology relates to a positioning and stabilising structure to hold a head-mounted display unit and an associated head-mounted display assembly including a display unit and positioning and stabilising structure. The present technology finds particular application in the use of virtual reality head-mounted displays and is herein described in that context. However, it is to be appreciated that the present technology may have broader application and may be used in other head-mounted display arrangements including augmented reality displays.

BACKGROUND OF THE TECHNOLOGY

It is to be understood that, if any prior art is referred to herein, such reference does not constitute an admission that the prior art forms a part of the common general knowledge in the art, in Australia or any other country.

Virtual reality head-mounted displays enable a user to have a fully immersive experience of a virtual environment and have broad application in fields such as communications, training, medical and surgical practice, engineering and video gaming.

Virtual reality head-mounted displays typically are provided as a system or assembly that includes a display unit which is arranged to be held in an operational position in front of a user's face. The display unit typically includes a housing containing a display and a user interface structure constructed and arranged to be in opposing relation with the user's face. The user interface structure may extend about the display and define a viewing opening to the display. The user interface structure may engage with the user's face and include a cushion for user comfort and/or be light sealing to cut ambient light from the display.

To hold the display unit in its correct operational position, the head-mounted display system further comprises a positioning and stabilising structure that is disposed on the user's head. In the past, these positioning and stabilising structures have been formed from straps or expandable rigid structures that are typically applied to the user's head under tension to maintain the display unit in its operational position. Such systems have been prone to exert a clamping pressure on the user's face which can result in user discomfort at localised stress points. Also, previous systems may be difficult to adjust to allow wide application head sizes. Further, the display unit and associated positioning and stabilising structure are often heavy and difficult to clean, which further limit the comfort and usability of the system.

Thus, there is a need for an improved system that does not suffer from the above-mentioned drawbacks.

BRIEF SUMMARY OF THE TECHNOLOGY

An aspect of the present technology relates to a positioning and stabilising structure for a head-mounted display unit including a rear support structure arranged, in use, to contact regions of the user's head, and opposing temporal connectors that are disposed on opposing sides of the user's head in use, and extending along the temporal regions of the user's head in use, to interconnect the rear support structure to the display unit.

In some forms, the rear support structure includes a hoop having an occipital portion and a parietal portion. In some forms, the hoop or at least one of the occipital and parietal portions may be resiliently extensible along at least a portion of its length. In some forms, the hoop is flexible along at least a portion of its length. In some forms, where the rear support structure is a hoop, the occipital portion may extend low on the user's head such that it resists upward movement (as a result of its location in contact with the occipital region of the head) and as such provides an anchor for the system. In some forms, the hoop is orientated in a generally upright plane (such upright plane including, as an example, the coronal plane).

In some forms, the rear support structure is disposed posterior to the otobasion superior of the user.

In some forms, the temporal connectors are rigid along at least a portion of their length. In some forms, the temporal connectors each comprise a temporal arm having an anterior end connected to the display unit and a posterior end connected to the rear support structure. In some forms, the temporal arm is rigid. In some forms, the posterior end of the temporal arm is disposed posterior to the otobasion superior of the user.

In some forms, at least one of the temporal connectors further comprises an adjustment mechanism for adjustment of the positioning and stabilising structure to fit different size heads. In some forms, the adjustment mechanism is disposed at the connection between the posterior end of the temporal arm and the rear support structure.

In some forms, the rear support structure comprises a connection tab that connects to the temporal arm, and the adjustment mechanism allows for adjustment of the effective length of the connection tab. In some forms, a posterior end of the temporal arm incorporates an eyelet that is arranged to receive the connection tab, the adjustment mechanism comprising a releasable fastening arrangement to fasten the connection tab to the temporal arm. In some forms, the releasable fastening arrangement may be arranged to secure a free end of the connection tab back onto a proximal portion of the connection tab. The releasable fastening arrangement may take other forms, such as clips or retainers that allow a friction, interference, snap or other mechanical fixing arrangement.

In some forms, the positioning and stabilising structure may further include a forehead support connector that extends generally in the direction of the sagittal plane and connects the rear support structure to a superior edge region of the display unit. In some forms, the forehead support connector may comprise a strap. In some forms, the strap of the forehead support connector may be resiliently extensible along at least a portion of its length. In some forms, the strap of the forehead support connector may be flexible along at least a portion of its length.

In some forms, the forehead support connector may further include an adjustment mechanism for adjustment of the positioning and stabilising structure to fit different size heads. In some forms, the adjustment mechanism may adjust the effective length of the strap of the forehead support connector when the forehead support connector is in that form.

In some forms, the forehead support connector further comprises a forehead support rigidiser that provides rigidification to a portion of the forehead support connector. In some forms, the forehead support rigidiser provides rigidification to a portion of the forehead support connector located along the frontal region of the user's head. The extent and positioning of the forehead support rigidiser may assist in correct positioning of the display unit and relieve pressure being applied to the zygomatic bone of the user. In some forms, the forehead support rigidiser may be adjustable (angularly or translational) on other components of the forehead support connector, such as the strap of the forehead support connector, to allow fine positioning of the head-mounted display unit and assist in improving user comfort and fit.

In some forms, the positioning and stabilising structure further includes additional rigidisers which may bridge the rear support structure and the temporal connectors. In some forms, these additional rigidisers may assist in controlling the movement of the display unit about the rear support structure to further stabilise and support the system. In some forms, these additional rigidisers may limit hinging movement at the connection of the temporal connectors to the rear support structure. In some forms, these additional rigidisers may also extend through along the occipital region of the rear support structure to further anchor the display unit in its correct operational position. In some forms, these additional rigidisers may be adjustable (angularly or translational) on other components of the forehead support connector to further assist in comfort, adjustability, and fit.

In some forms, the positioning and stabilising structure may allow for upward, e.g., superior, pivoting movement of the display unit to allow for movement of the display unit to a non-operational position without removal of the positional and stabilising structure (e.g., flip-up version). In some forms, this pivoting arrangement may provide a release mechanism at the forehead support connector and/or provide limited hinging regions at the temporal connectors.

The positioning and stabilising structure in any form described above may be incorporated in a hood or other head wear either integrated therein or releasably connected thereto. The positional and stabilising structure may also include other components integrated therein such as audio, tactile (haptic) stimulation or feedback.

An aspect of the present technology relates to a head-mounted display system including a head-mounted display unit and a positioning and stabilising structure structured and arranged to hold the head-mounted display unit in an operational position over a user's face in use. The positioning and stabilising structure includes a rear support structure adapted to contact posterior regions of a user's head and at least one connector structured and arranged to interconnect the rear support structure to the head-mounted display unit. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to a positioning and stabilising structure to hold a head-mounted display unit in an operational position over a user's face. The positioning and stabilising structure includes a rear support structure adapted to contact posterior regions of a user's head and at least one connector structured and arranged to interconnect the rear support structure to the head-mounted display unit. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to a positioning and stabilising structure to hold a head-mounted display unit in an operational position over a user's face. The positioning and stabilising structure includes a rear support structure adapted to contact posterior regions of a user's head and opposing temporal connectors structured and arranged to interconnect the rear support structure to the head-mounted display unit. The opposing temporal connectors are adapted to be disposed on opposing sides of the user's head and extend along the temporal regions of the user's head. The rear support structure is in the form of a hoop comprising an occipital portion configured and arranged engage the user's head along the occipital bone (e.g., along a portion of the occipital bone adjacent a junction where the neck muscles attach to the occipital bone) in use.

An aspect of the present technology relates to a head-mounted display system including a head-mounted display unit and a positioning and stabilising structure structured and arranged to hold the head-mounted display unit in an operational position over a user's face in use. The positioning and stabilising structure includes a rear support structure adapted to contact posterior regions of a user's head and at least one connector structured and arranged to interconnect the rear support structure to the head-mounted display unit. At least the rear support structure comprises a textile material configured to conform to the posterior regions of the user's head.

An aspect of the present technology relates to a positioning and stabilising structure to hold a head-mounted display unit in an operational position over a user's face. The positioning and stabilising structure includes a rear support structure adapted to contact posterior regions of a user's head and at least one connector structured and arranged to interconnect the rear support structure to the head-mounted display unit. At least the rear support structure comprises a textile material configured to conform to the posterior regions of a user's head.

An aspect of the present technology relates to a head-mounted display system including a head-mounted display unit and a positioning and stabilising structure structured and arranged to hold the head-mounted display unit in an operational position over a user's face in use. The positioning and stabilising structure includes a rear support structure adapted to contact posterior regions of a user's head and opposing temporal connectors structured and arranged to interconnect the rear support structure to the head-mounted display unit, the opposing temporal connectors adapted to be disposed on opposing sides of the user's head and extend along the temporal regions of the user's head. At least the rear support structure comprises a textile material configured to conform to the posterior regions of the user's head.

An aspect of the present technology relates to a positioning and stabilising structure to hold a head-mounted display unit in an operational position over a user's face. The positioning and stabilising structure includes a rear support structure adapted to contact posterior regions of a user's head and opposing temporal connectors structured and arranged to interconnect the rear support structure to the head-mounted display unit, the opposing temporal connectors adapted to be disposed on opposing sides of the user's head and extend along the temporal regions of the user's head. At least the rear support structure comprises a textile material configured to conform to the posterior regions of the user's head.

An aspect of the present technology relates to a positioning and stabilising structure to hold a head-mounted display unit in an operational position over a user's face. The positioning and stabilising structure includes a rear support structure adapted to contact regions of a user's head and at least one connector or strap structured and arranged to interconnect the rear support structure to the head-mounted display unit.

The positioning and stabilizing structure and/or the head-mounted display unit may be configured to help distribute contact forces from more sensitive regions of the user's face (forehead, upper cheeks below the eyes) to regions that are better suited to oppose a force applied. For example, the rear support structure may be sufficiently flexible to evenly and snugly engage the rear of the user's head, e.g., anchor on the occipital bone but above the neck muscles, and/or have increased rigidity in one or more portions to better support the load of the head-mounted display unit in a comfortable and sustainable manner. For example, the rear support structure may be made of a strap material (e.g., textile) that is breathable and flexible to allow it to adjust to the shape and/or size of the user's head, where certain parts of the strap material may be rigidized and/or a rigid portion added (e.g., sewn, laminated, clipped, inserted into a pocket, overmolded, and/or ultrasonically welded into place) to help maintain stability and offset a portion of the force applied to a portion of the patient's face via the head-mounted display unit.

In an example, the positioning and stabilizing structure and/or the head-mounted display unit may be configured to cooperatively work together to reduce the force applied to the patient's forehead and/or cheek bones, by effectively transferring those forces to the rear support and/or to the at least one connector or strap(s), and/or by simply distributing the forces from the head-mounted display unit more evenly along the head-mounted display unit and/or the rear support structure and/or the at least one connector or strap(s). This is done in a way that adds comfort and/or stability, e.g., to prevent the head-mounted unit from sliding down the user's face/forehead.

Another aspect of the present technology relates to a head mounted-display system or assembly including a positional and stabilising structure in any form described above, and a display unit connected thereto.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Figure 1A:
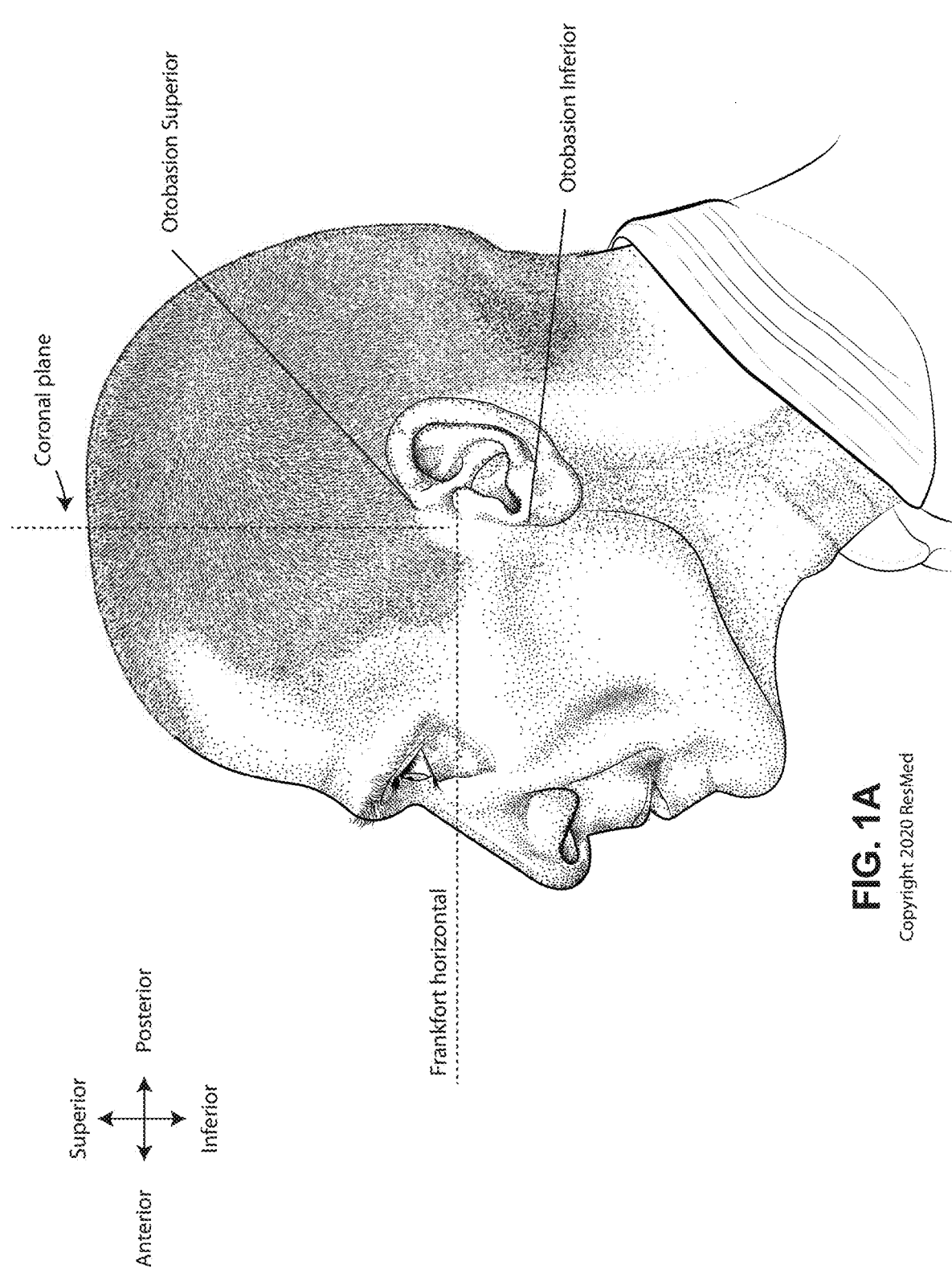
FIG. 1A is a side view of a head with several features of surface anatomy identified including otobasion superior and otobasion inferior. The approximate location of the Frankfort horizontal is indicated. The coronal plane is also indicated. Also indicated are the directions superior & inferior, and anterior & posterior.
Figures 1B, 1C:
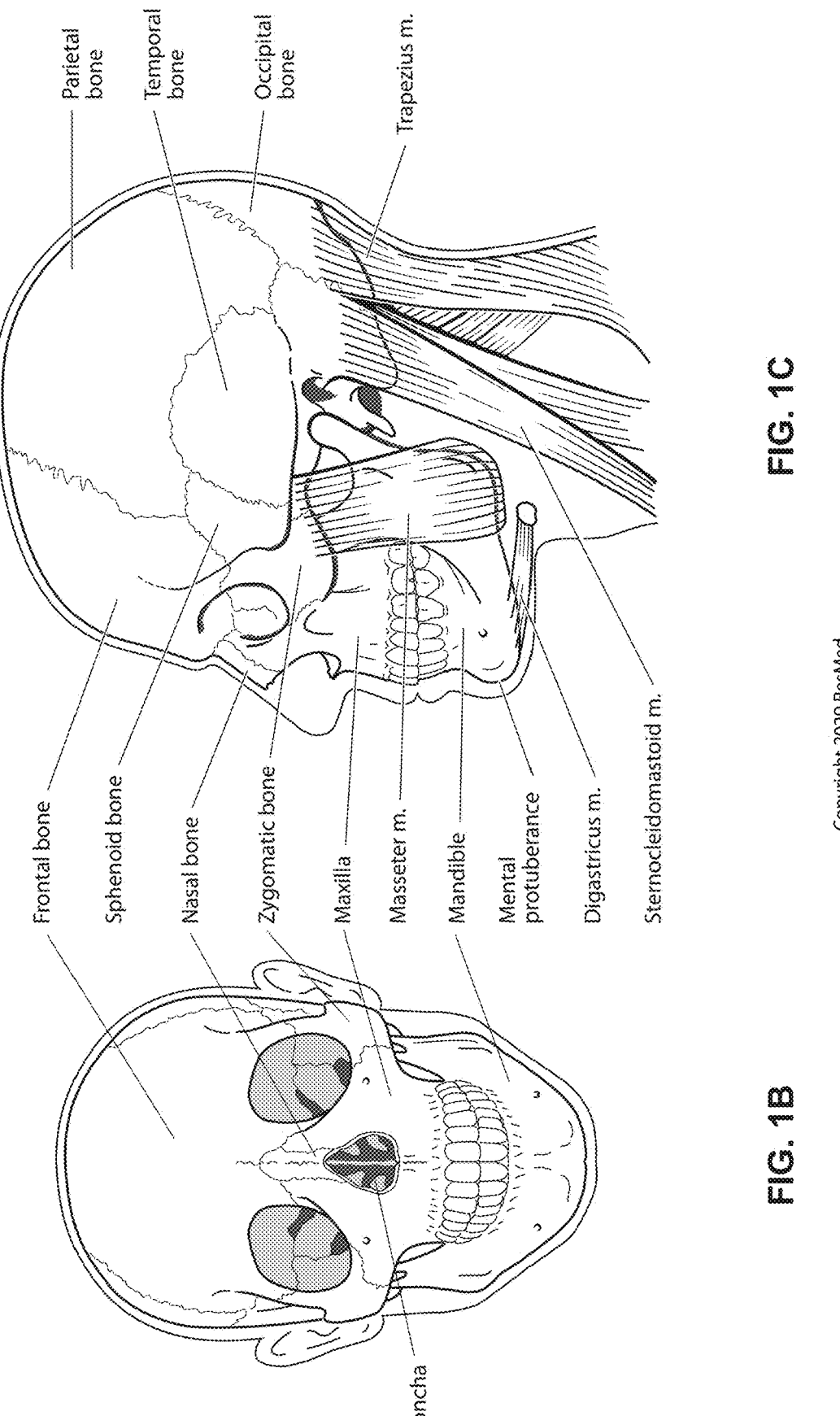
FIG. 1B shows a front view of the bones of a skull including the frontal, nasal and zygomatic bones.
FIG. 1C shows a lateral view of a skull with the outline of the surface of a head, as well as several muscles. Exemplary bones shown include frontal, sphenoid, nasal, zygomatic, maxilla, mandible, parietal, temporal and occipital.
Figure 2A:
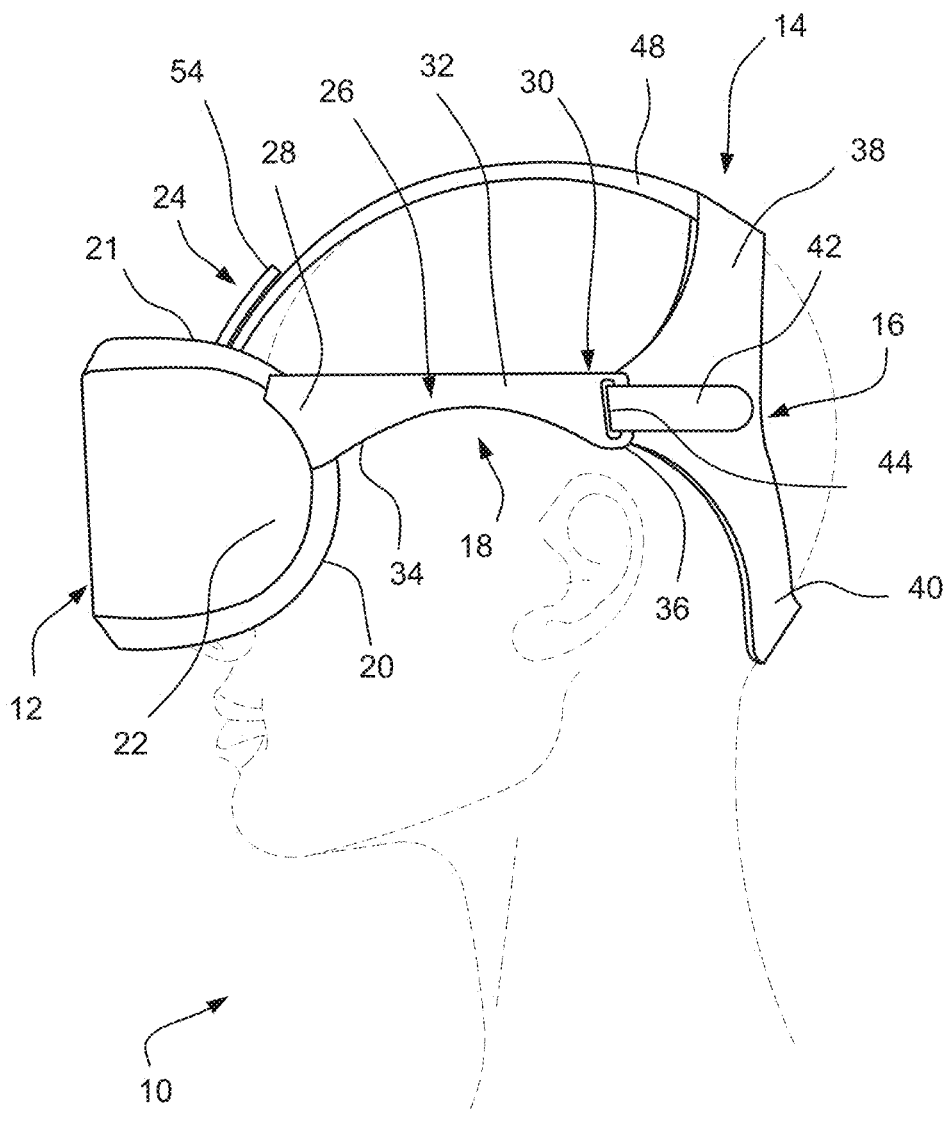
FIGS. 2A to 2C are respective side, front and top views of a head-mounted display assembly in-use according to a first example of the present technology.
Figure 2B:
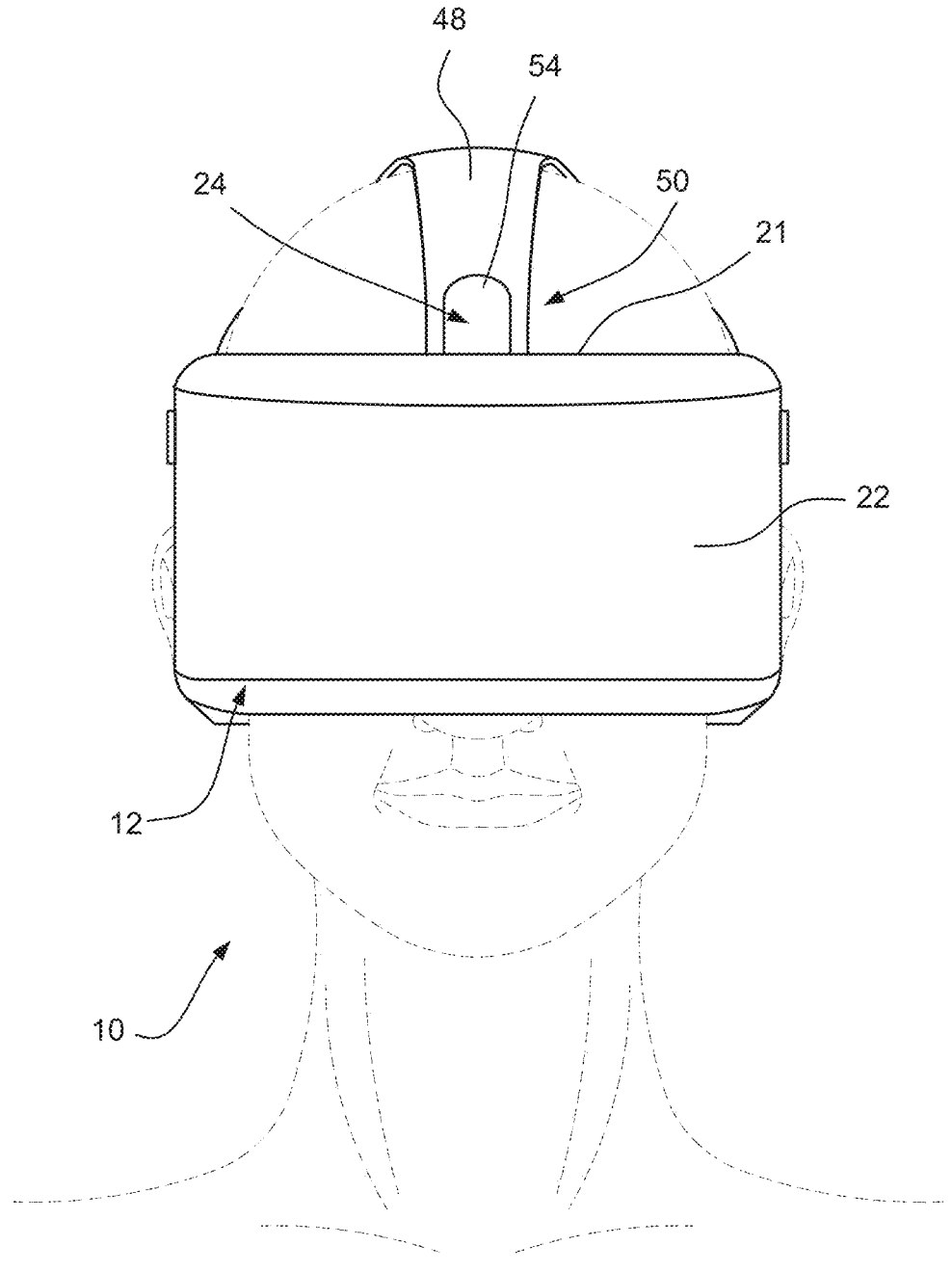
Figure 2C:
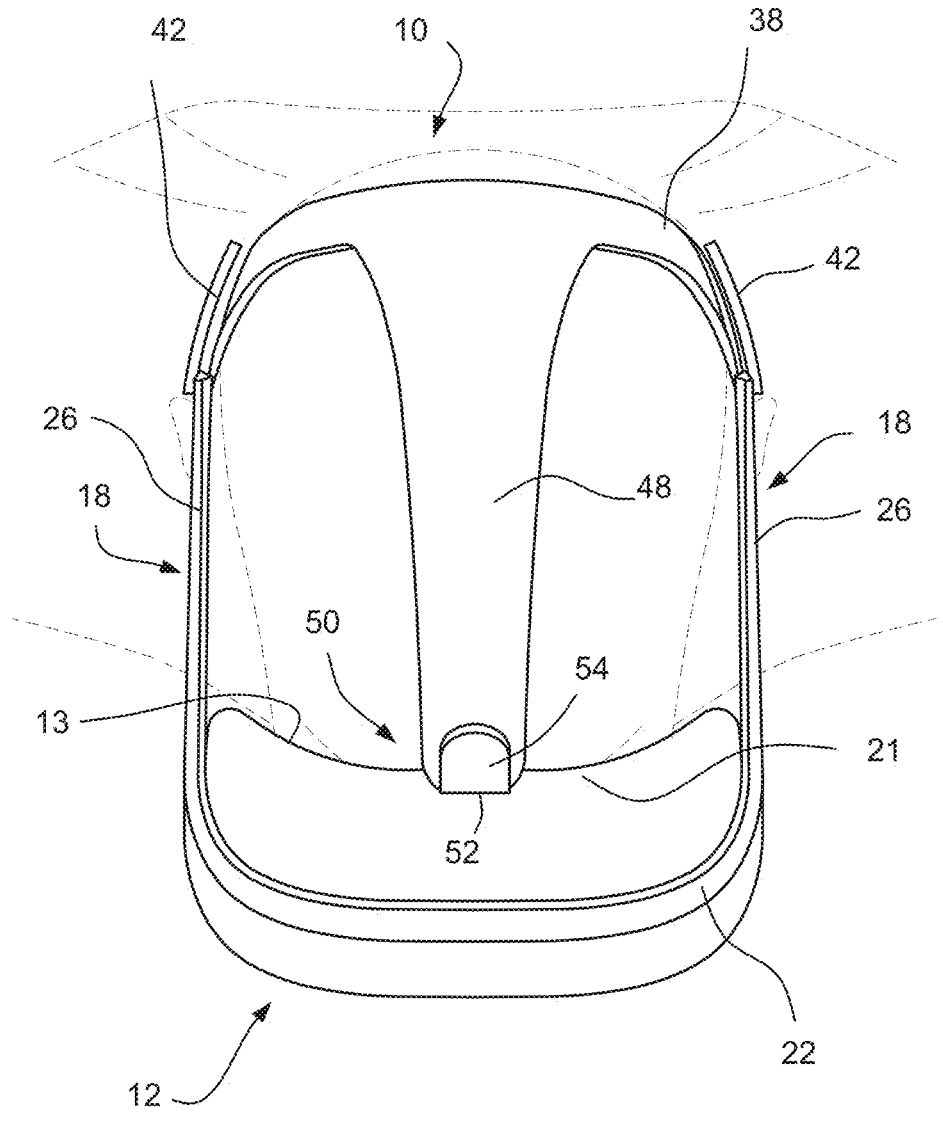

FIGS. 2A to 2C show a support for a head-mounted display system or assembly 10 according to a first example of the present technology. The head-mounted display system 10 comprises a head-mounted display unit 12, and a positioning and stabilising structure 14 (also referred to as a support and stabilising structure) to maintain or hold the display unit 12 in an operational position over a user's face in use.

The display unit 12 includes a user interface structure 13 constructed and arranged to be in opposing relation with the user's face. The user interface structure 13 extends about a display contained by the display unit housing 22. The user interface structure 13 may extend about the display and define a viewing opening to the display. The user interface structure 13 extends around the user's eyes, and may engage (e.g., light sealing) with the user's face, e.g., along the user's nose, cheeks and/or forehead.

As described below, the head-mounted display system according to examples of the present technology is structured and arranged to provide a balanced system, i.e., not overly tight at any singular point along the user's head and/or face, while providing a perception of complete sealing around the user's eyes, i.e., to provide complete immersion in the use of virtual reality head-mounted displays. That is, the head-mounted display system according to examples of the present technology provides a more even fit that is structured and arranged to distribute pressure over more of the user's head to lessen hot spots or localised stress points.

Also, the head-mounted display system according to examples of the present technology comprises soft and flexible (e.g., elastic) materials (e.g., breathable material, e.g., textile-foam composite) structured and arranged to allow more conformity to the user's head and cushioning for comfort. In addition, the head-mounted display system according to examples of the present technology comprises simple adjustment mechanisms to facilitate adjustment while on the user's head and allow a wide fit range.

In the illustrated example of FIGS. 2A to 2C, the positioning and stabilising structure 14 comprises a rear support structure 16 (also referred to as a rear support hoop) adapted to contact regions of a user's head (e.g., positionable at a crown of the user's head) and at least one connector structured and arranged to interconnect the rear support structure 16 to the head-mounted display unit 12. In the illustrated example, the at least one connector comprises opposing temporal connectors 18 disposed on respective sides of the user's head that interconnect the rear support hoop 16 to respective posterior edge regions 20 of the display unit housing 22 of the display unit 12, and a forehead support connector 24 that extends across the frontal bone of the user to interconnect the rear support hoop 16 with a superior edge region 21 of the display unit housing 22. However, it should be appreciated that more or less connectors may be provided to interconnect the rear support structure 16 to the head-mounted display unit 12.

Each of the opposing temporal connectors 18 comprises a temporal arm 26. Each temporal arm 26 includes an anterior end 28 mounted to the respective posterior edge region 20 of the display unit housing 22 and a posterior end 30 that forms part of a releasable coupling to connect the temporal arm 26 to the rear support hoop 16.

Each temporal arm 26 comprises a rigidiser 32, a textile component 34 and a tab 36 arranged at the posterior end 30 for connecting to the rear support hoop 16. In an example, a portion of each of the temporal arms 26, in-use, is in contact with a region of the user's head proximal to the otobasion superior, i.e., above the user's ear. In an example, the temporal arms 26 are arranged in-use to run generally along or parallel to the Frankfort Horizontal plane of the head and superior to the zygomatic bone, i.e., above the user's cheek bone.

Figure 2D:
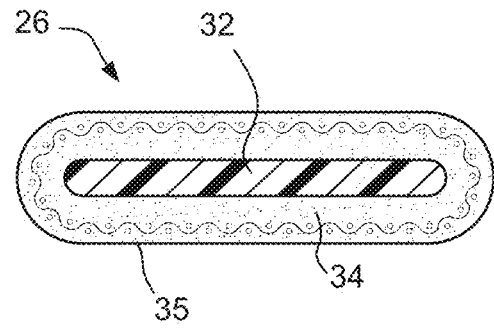
FIG. 2D is a cross-sectional view of a temporal arm of the head-mounted display assembly of FIGS. 2A to 2C according to an example of the present technology.
Figure 2E:
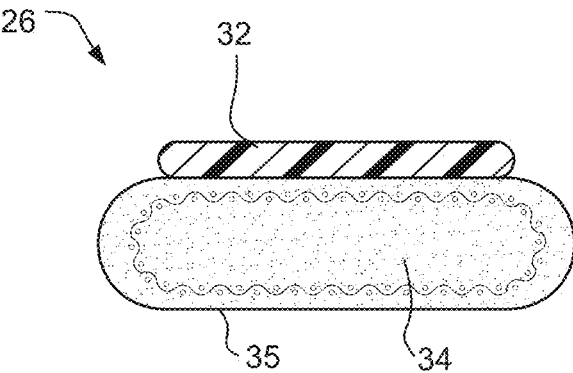
FIG. 2E is a cross-sectional view of a temporal arm of the head-mounted display assembly of FIGS. 2A to 2C according to another example of the present technology.

In one form, the rigidiser 32 may be encapsulated within the textile component 34 of each temporal arm 26. For example, FIG. 2D shows an example of the textile component 34 in the form of a cover configured to encapsulate the rigidiser 32. In this example, the textile component 34 includes a face contacting side arranged on one side of the rigidiser 32 that can provide a soft, face contacting surface 35 adapted to contact the patient's face in use. In some alternative forms, the rigidiser 32 may be stitched or otherwise attached (e.g., overmolded) to the textile component 34, or the textile component can be made of materials that can be selectively rigidised by heat treatment (e.g., heat treatment). For example, FIG. 2E shows an example of the textile component 34 attached to a face contacting side of the rigidiser 32 that can provide a soft, face contacting surface 35 adapted to contact the patient's face in use. In an example, the textile component 34 may comprise a textile material or a textile-foam composite (e.g., breathable material, e.g., multi-layered construction including an outer textile layer and an inner foam layer) to provide a soft support for the rigidiser 32 to cushion against the user's head for optimised comfort. The rigidiser 32 can allow each temporal arm 26 to retain an in-use shape and configuration when not worn by a user. Advantageously, maintaining the temporal arms 26 in the in-use state prior to use may prevent or limit distortion whilst the user is donning the positioning and stabilising structure 14 and allow a user to quickly fit or wear the display system 10.

In an example, the rigidiser 32 can be made from a rigid material, e.g., hytrel (thermoplastic polyester elastomer). As such, the rigidiser 32 (or the temporal connector 18 or the temporal arm 26) is rigid along at least a portion of its length. The rigid nature, i.e., inextensibility, of the rigidiser 32 of each temporal arm 26 limits the magnitude of elongation or deformation of the temporal arm 26 while in-use. Advantageously, this configuration enables a more effective, i.e., direct, translation of tension through the temporal arm 26. In an example, the rigidiser 32 may be more rigid than the rear support hoop 16 and/or connection straps 42 (e.g., formed from an elastic and/or textile material). Consequently, the temporal arm 26 of each opposing temporal connector 18 may be more rigid than the other parts of the positioning and stabilising structure 14, such as more rigid than the rear support hoop 16 and/or connection straps 42. The temporal arm 26 (or temporal connector 18) may be more rigid along at least a portion of its length than the other parts of the positioning and stabilising structure 14, such as more rigid than the rear support hoop 16 and/or connection straps 42. For example, in contrast to the rigidiser 32 (or the temporal connector 18 or the temporal arm 26), the rear support hoop 16 and/or connection straps 42 may be stretchable to a desired length, i.e., resiliently extensible along at least a portion of its length.

In an example, the rigidiser 32 may be structurally rigid or stiff to resist bending deformation vertically up and down alongside the user's face, but may allow bending deformation towards and away from the user's face (e.g., to adjust for varying facial width). In an example, the rigidiser 32 may be structurally rigid or stiff to resist deformation under twisting. In an example, the rigidiser 32 may be structurally rigid or stiff to maintain a preformed shape.

In an example, the rigidiser 32 forms a lever-arm, i.e., a means to pivot, about the rear support hoop 16. Advantageously, the rear support hoop 16 can provide an anchor point for the positioning and stabilising structure 14. The rigidiser 32 may articulate about the anchor point of the rear support hoop 16 to enable the forehead support connector 24 to raise or lower the position of the display unit 12 relative to the user's nose. Advantageously, this configuration can minimise the magnitude of clamping pressure to stabilise the display unit 12 on the user's head.

In an example, the thickness and/or width of the temporal arm 26 may vary along at least a portion of its length, e.g., temporal arm 26 may include wider and thinner sections along its length to facilitate connection and to distribute load.

Figure 6A:
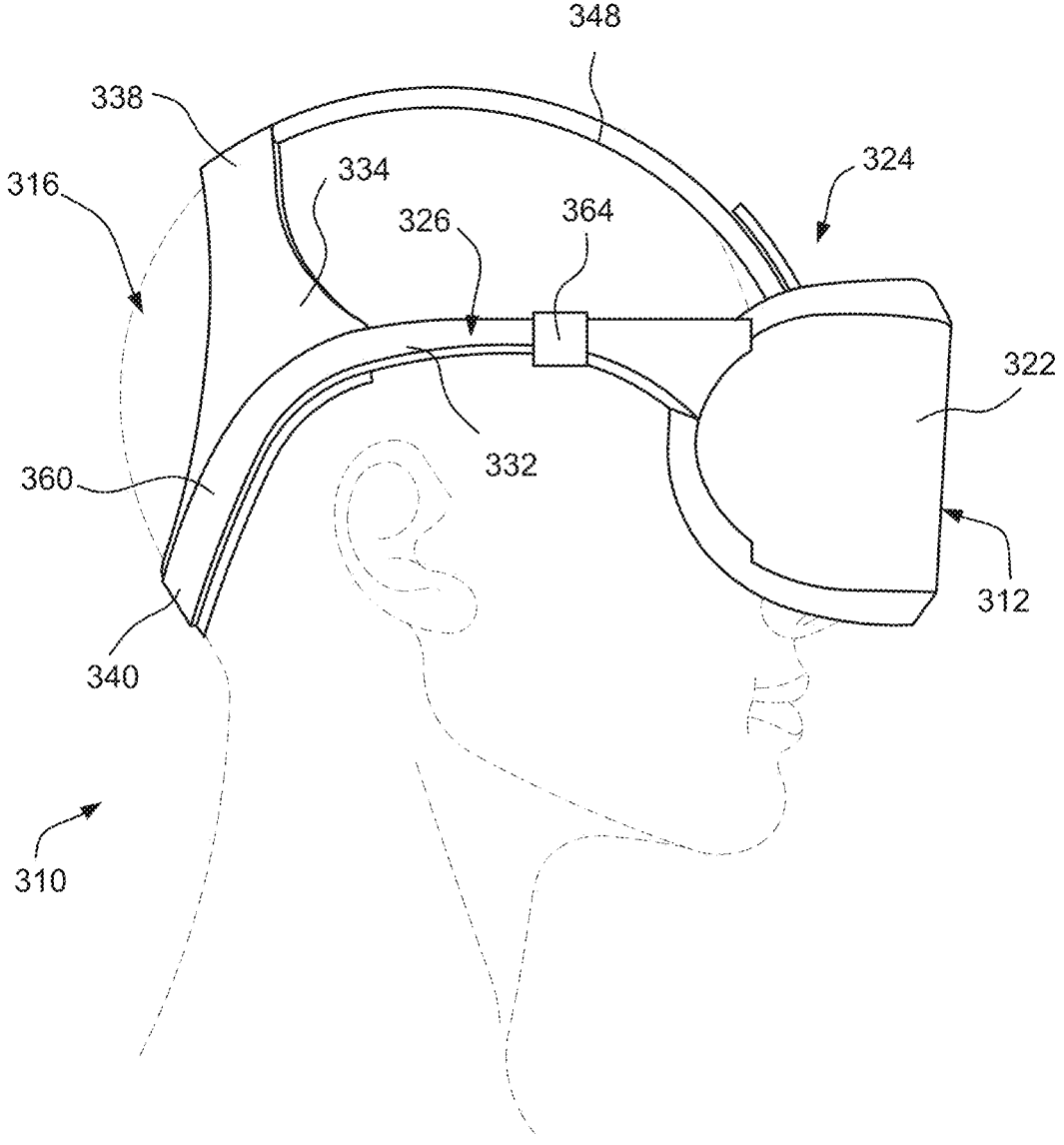
FIGS. 6A to 6C are respective side, rear and top views of a head-mounted display assembly in-use according to a variation of the fourth example of the present technology.
Figure 6B:
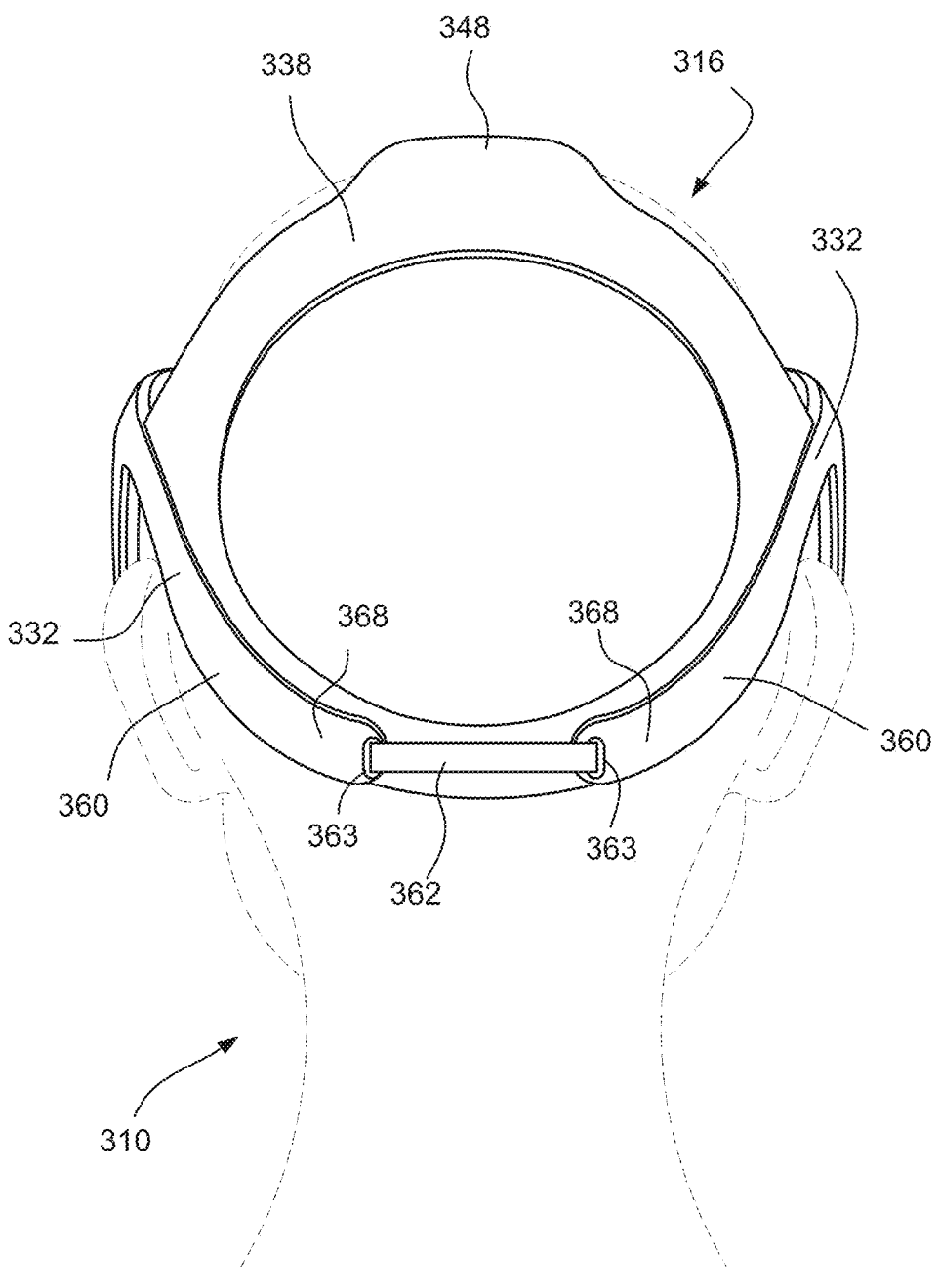

In the illustrated example, the rear support structure or hoop 16 is in the form of a hoop having a ring-like form (similar to the ring-like form of rear support hoop 316 shown in the FIG. 6B example) and is arranged to have a three-dimensional contour curve to fit or conform to the shape of the rear of the user's head, e.g., a user's crown. The rear support hoop 16 comprises a parietal portion or parietal strap portion 38, adapted to be in proximity to the parietal bone of the user's head in use, and an occipital portion or occipital strap portion 40, adapted to be in proximity to the occipital bone of the user's head in use. In an example, the occipital portion 40 is preferably arranged along a portion of the occipital bone in use, e.g., along a portion of the occipital bone adjacent or near a junction where the neck muscles attach, and the parietal portion 38 is preferably arranged rearward of the coronal plane in use. In an example, the occipital portion 40 is adapted to be positioned along a portion of the occipital bone just above a junction where the neck muscles attach to the occipital bone. The junction may also be referred to as the external occipital protuberance (EOP). However, the exact location of the occipital portion 40 on the user's head may vary depending on the size and shape of the user's head with which it is being used, e.g., the occipital portion 40 may be positioned adjacent to, just above, or just below a portion of the occipital bone where the neck muscles attach. In an example, the occipital portion 40 may be arranged beneath or underneath the occipital bone near the junction where the neck muscles attach. This hoop-like arrangement (e.g., circular or ovular or part circular/oval or C-shaped) of the rear support hoop 16 anchors the positioning and stabilising structure 14 around the rear or rear bump of the user's head, which provides an effective support structure to hold weight (i.e., the display unit) at the front of the user's head. The rear support hoop 16 may be formed from an elastic material, which elasticity may be used to stretch the hoop and securely hold the rear support hoop 16 in position.

The rear support hoop 16 further comprises opposing connection straps or tabs 42. The straps 42 are adjustable and operate to change the distance between the rear support hoop 16 and the display unit housing 22 of the display unit 12. Each of the straps 42, in use, is threaded through an eyelet 44 in the tab 36 of a respective temporal arm 26. The length of each strap 42 through the tab 36 of a respective temporal connector 18 may be adjusted by pulling more or less of the strap 42 through a respective eyelet 44. The strap 42 may be secured to itself after passing through the eyelet 44 in the tab 36, for example, with hook-and-loop fastening means, which allows fine or micro adjustment of the straps for comfort and fit (e.g., tightness). Therefore, the distance between the rear support hoop 16 and the display unit housing 22 may be adjusted to fit around different head sizes. Such adjustable strap arrangement also allows adjustment while the system is on the user's head, e.g., user can pull straps 42 to posteriorly tighten.

In an example, the thickness and/or width of the rear support hoop 16 and/or the straps 42 may vary along at least a portion of its length. For example, the rear support loop 16 may include wider and thinner sections along its length, e.g., wider sections adjacent the straps 42 to facilitate connection to the temporal arms 26 and to distribute load. Also the straps 42 may be thinner along it free end to facilitate threading through the eyelet 44 in the respective temporal arm 26.

In an example, the rear support hoop 16 is orientated in a generally vertical direction, i.e., arranged in a vertical plane generally parallel to the coronal plane. This arrangement of the rear support hoop 16 appropriately orients the rear support hoop 16 at the crown of the user's head to support the transverse, i.e., horizontal, tension applied by the connection straps 42 and support the weight of the display unit 12, in-use, at the anterior of the user's head.

The rear support hoop 16 and connection straps 42 may be formed from an elastic and/or textile material to assist conforming to the shape of a user's head, e.g. rear support hoop 16 and connection straps 42 provide stretch capacity. Also, such elastic material at the back of the user's head may allow easier lifting of the display unit 12 away from the user's face in use, e.g., move the display unit 12 away from the user's eyes to talk to someone while the positioning and stabilising structure 14 remains on the user's head. For example, the support hoop 16 may be a neoprene material, or other textile-foam composite (e.g., breathable material, e.g., multi-layered construction including at an outer textile layer and an inner foam layer), or spacer fabric. Advantageously, textiles can provide a soft support structure to stabilise the display unit 12 on a user's head and allow the positioning and stabilising structure 14 to cushion against the user's head for optimised comfort.

The forehead support connector 24 of the positioning and stabilising structure 14 comprises a forehead support strap 48 arranged to run generally along or parallel to the sagittal plane of the user's head. The forehead support strap 48 is adapted to connect between the superior edge region 21 of the display unit housing 22 and the parietal portion 38 of the rear support hoop 16. In an example, the strap 48 can be non-adjustably connected, e.g., welded, to the parietal portion 38, and the strap 48 can be adjustably connected to the display unit housing 22 by an adjustment mechanism 50.

The forehead support strap 48 is adjustable to enable dimensional control of the forehead support connector 24. As best shown in FIG. 2C, an end portion or tab portion 54 of the forehead support strap 48, in use, is threaded through a forehead support hole 52 in the superior edge region 21 of the display unit 12. The forehead support strap 48 may be secured to itself after passing through the hole 52 in the display unit 12, for example, with hook-and-loop fastening means, which allows fine or micro adjustment of the straps for comfort and fit (e.g., tightness). In an example, the forehead support strap 48 may comprise a similar material to rear support hoop 16 and/or the connection straps 42, e.g., textile-foam composite (e.g., breathable material, e.g., multi-layered construction including at an outer textile layer and an inner foam layer).

The forehead support connector 24 supports the weight of the display unit 12. The length of the forehead support strap 48 between the superior edge region 21 of the display unit 12 and the parietal portion 38 of the rear support hoop 16 may be adjusted by pulling more or less of the strap 48 through the hole 52. Therefore, the forehead support strap 48 is able to be adjusted to raise or lower the position of the display unit 12 relative to the user's nose, e.g., adjust to angle or lift the display unit 12 relative to the user's face. Advantageously, this adjustment can move the display unit housing 22 away from the user's nose to relieve pressure felt on the face, nose, and/or cheeks. The forehead support connector 24 secures the display unit 12 in position so that the display unit does not slide downwards or laterally on the user's head.

In an example, the thickness and/or width of the forehead support strap 48 may vary along at least a portion of its length, e.g., forehead support strap 48 may include wider and thinner sections along its length to facilitate connection and to distribute load.

In an example, the adjustment mechanism 50 is positioned, in use, out of contact with a user's frontal bone region.

Figure 4A:
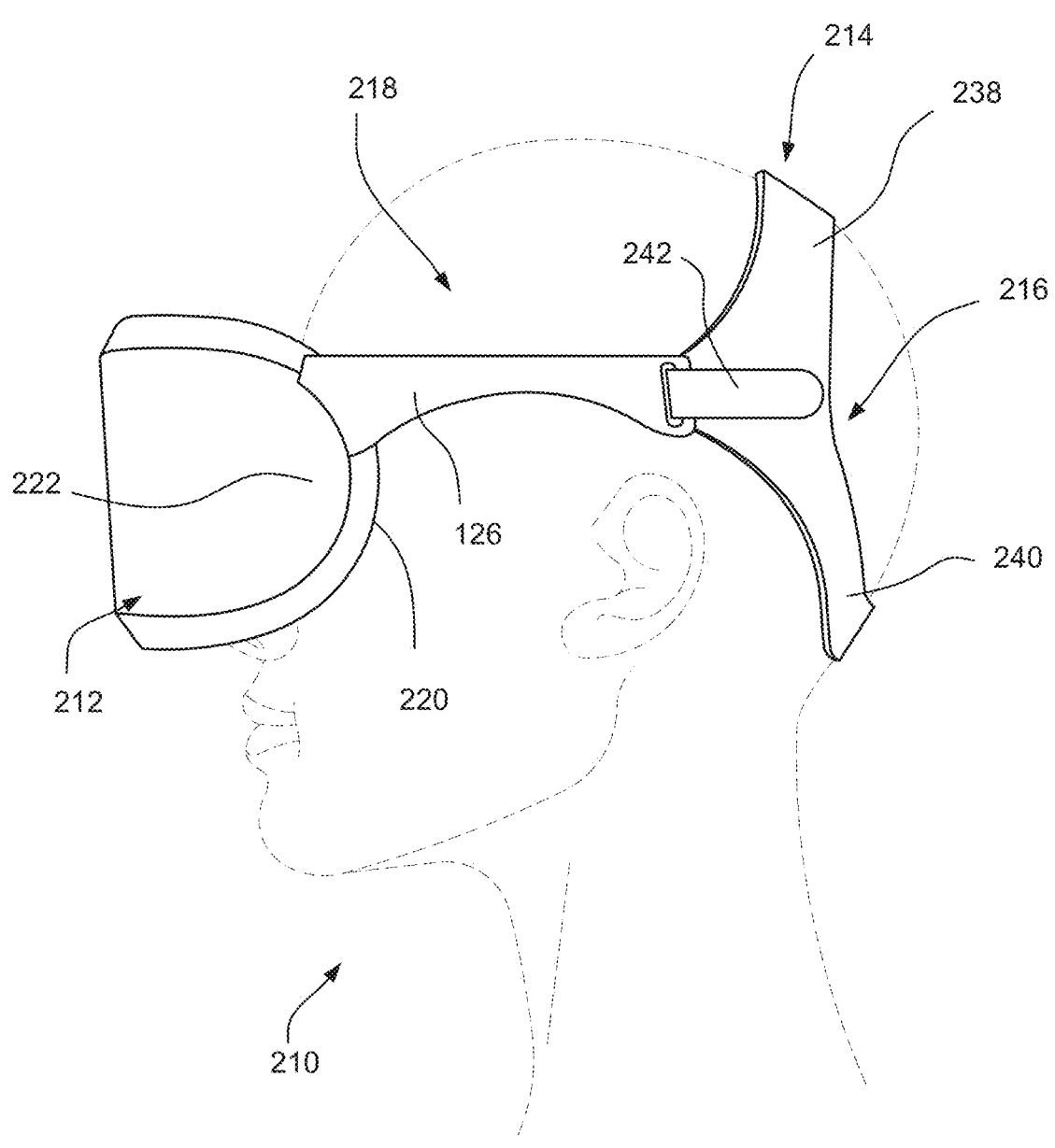
FIGS. 4A to 4C are respective side, front and top views of a head-mounted display assembly in-use according to a third example of the present technology.
Figure 4B:
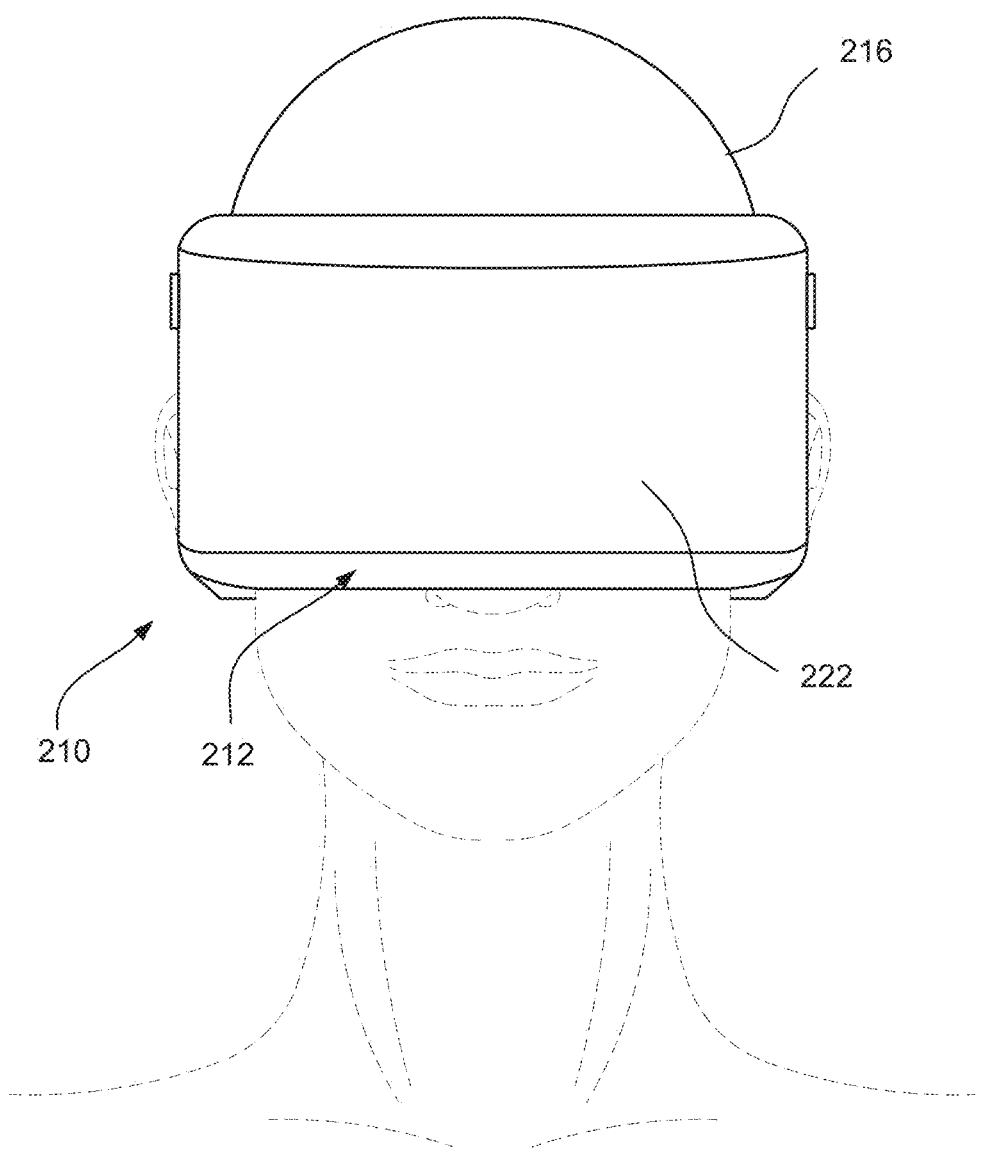
Figure 4C:
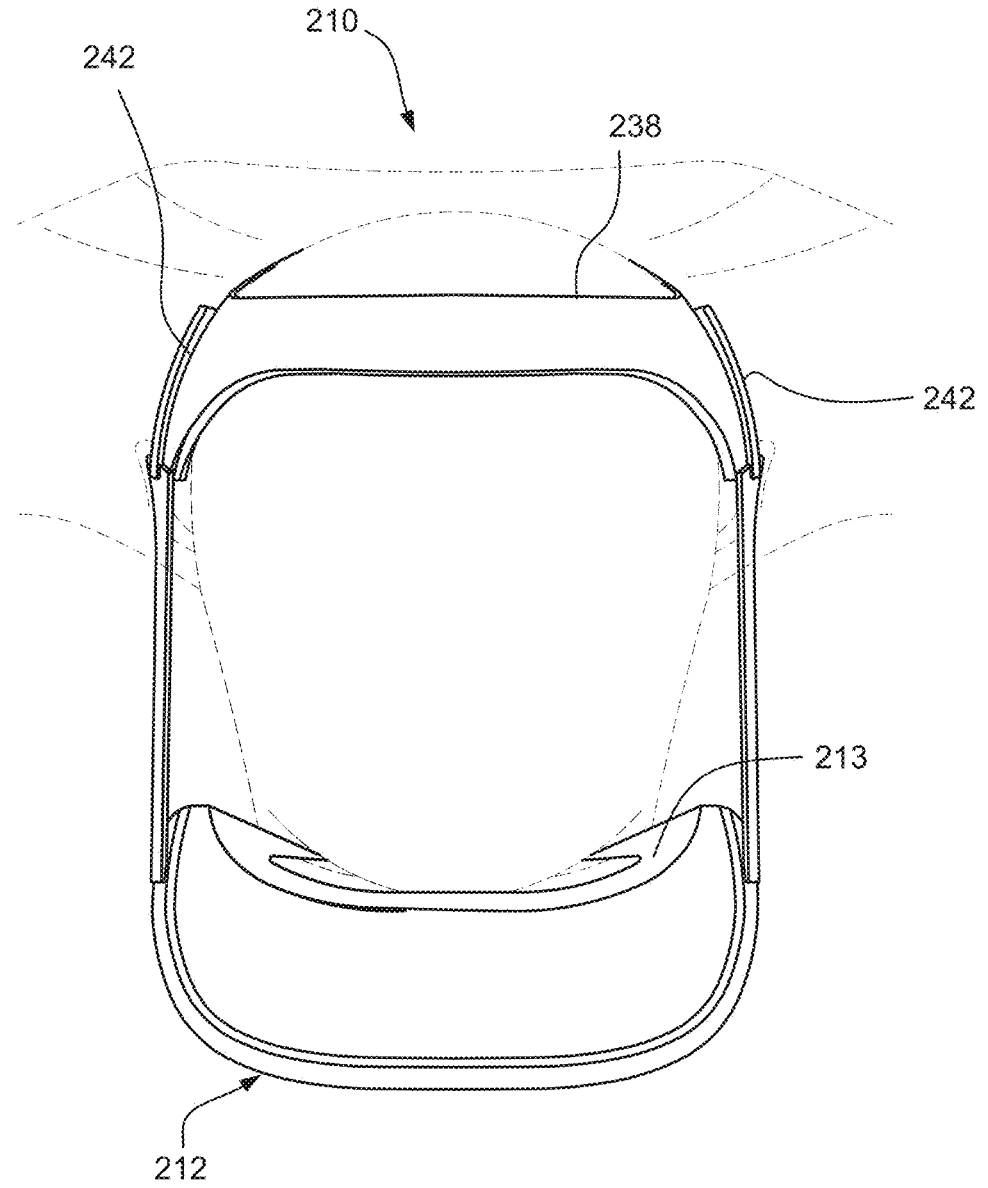

In an alternative example, the positioning and stabilising structure 14 does not include a forehead support connector 24/forehead support strap 48, e.g., see example of FIGS. 4A to 4C.

Figure 3A:
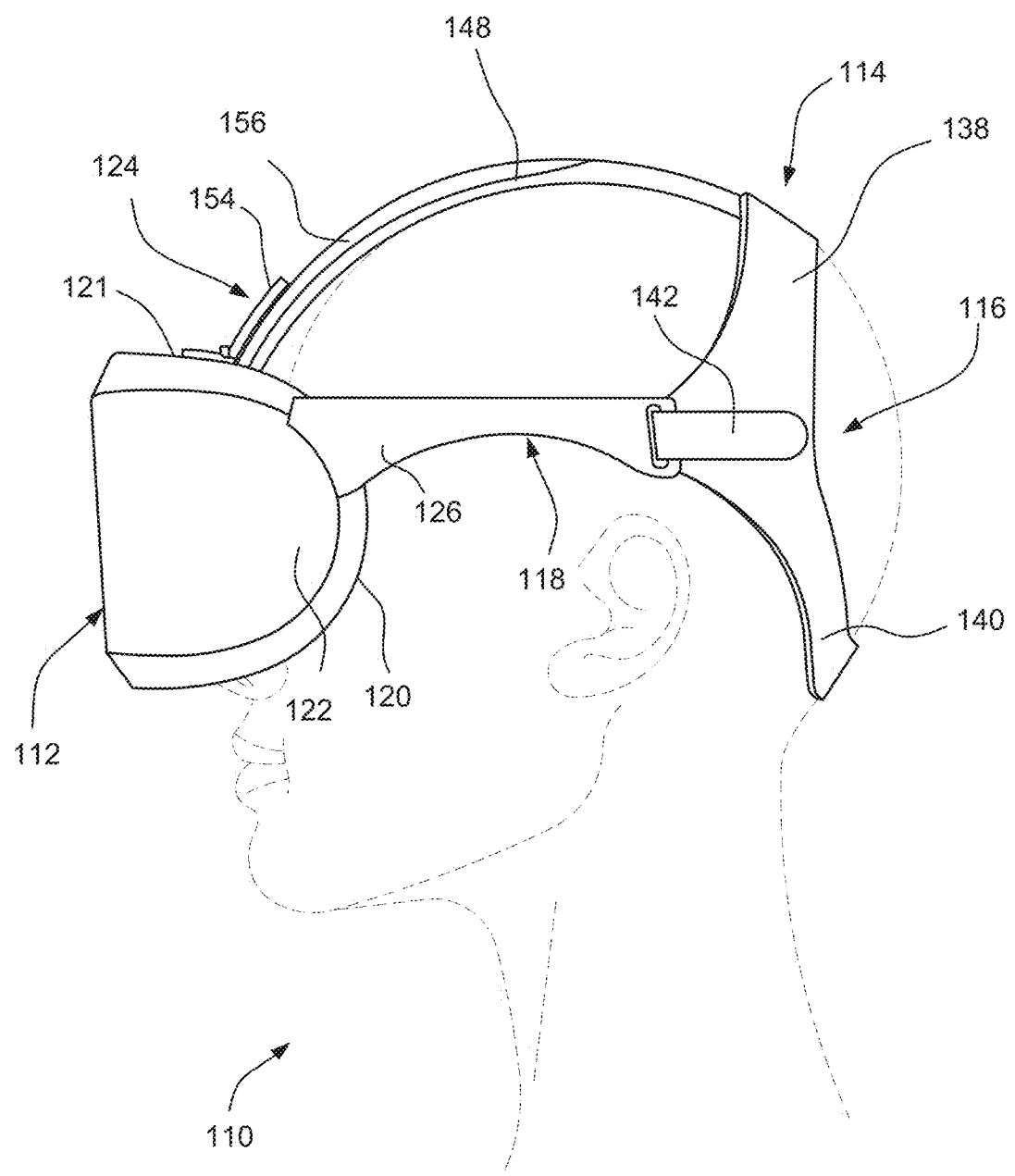
FIGS. 3A to 3C are respective side, front and top views of a head-mounted display assembly in-use according to a second example of the present technology.
Figure 3B:
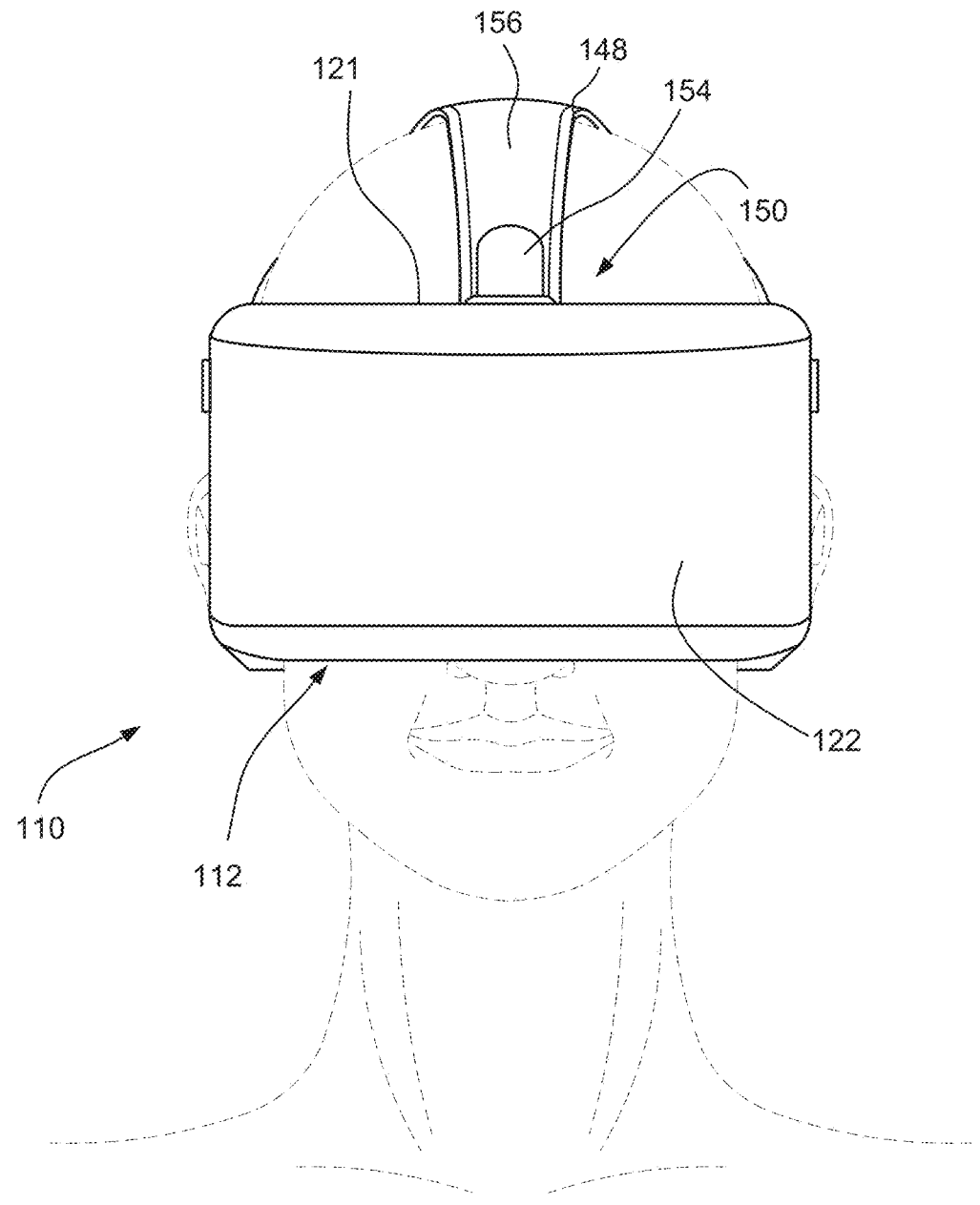
Figure 3C:
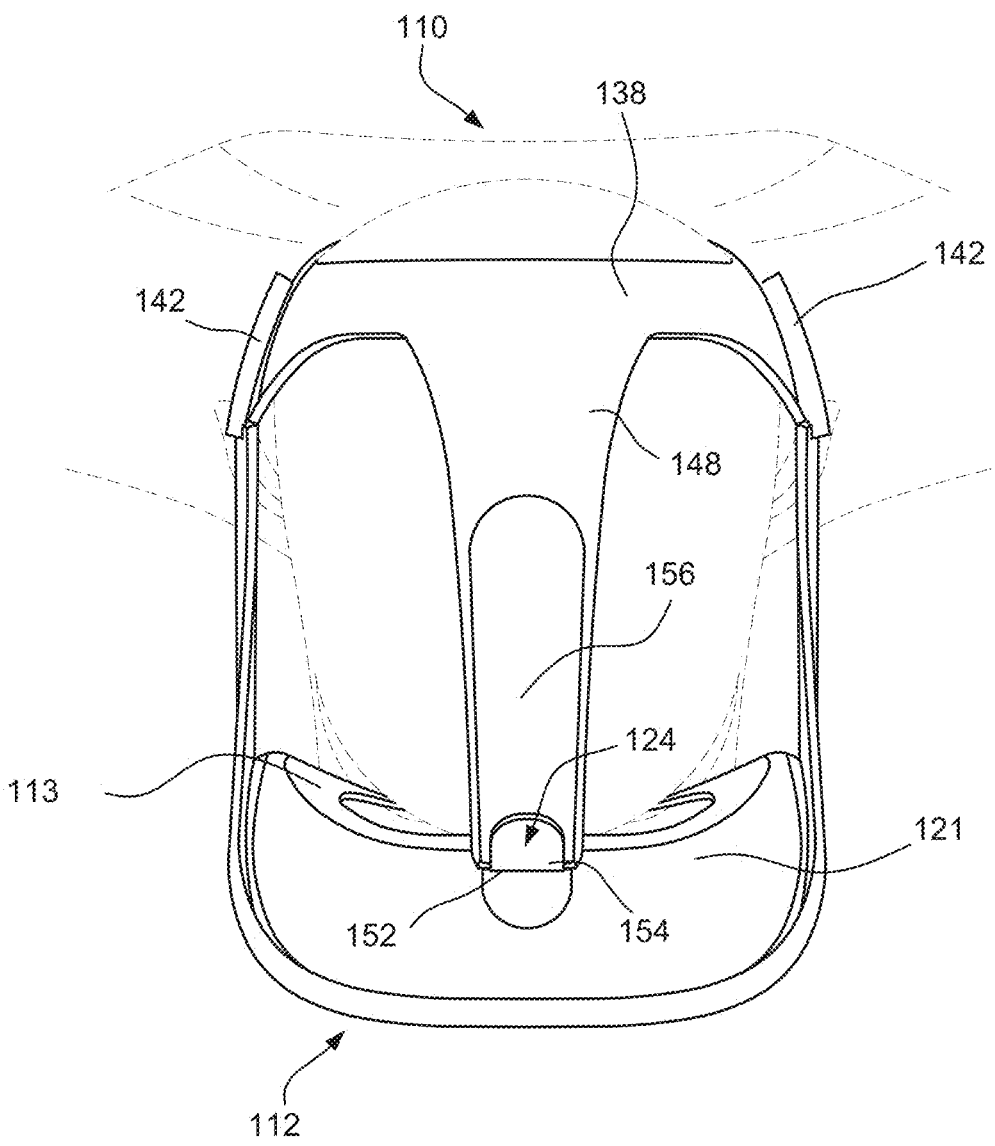

FIGS. 3A to 3C show a support for a head-mounted display system or assembly 110 according to a second example of the present technology. In FIGS. 3A to 3C, like reference numerals denote similar or like parts to FIGS. 2A to 2C with the addition of 100 to allow distinguishing between examples, e.g., display unit 112, user interface structure 113, positioning and stabilizing structure 114, rear support hoop 116, temporal connector 118, posterior edge region 120, display unit housing 122, forehead support connector 124, temporal arm 126, parietal portion 138, occipital portion 140, connection straps 142, forehead support strap 148, adjustment mechanism 150, forehead support hole 152, end portion 154. Referring to FIG. 3C, the forehead support connector 124 may further comprise a forehead support rigidiser 156. The forehead support rigidiser 156 can provide further stabilisation and support for the display unit 112 above the user's nose and cheeks, i.e., relieve pressure on the user's nose and cheeks. The forehead support rigidiser 156 can be connected to the superior edge region 121 and form at least part of the forehead support hole 152 to receive an end portion or tab portion 154 of the forehead support strap 148 for dimensional adjustment of the positioning and stabilising structure 114. As illustrated the forehead support strap 148 is arranged beneath the forehead support rigidiser 156 for comfort and load distribution.

In some forms, the adjustment mechanism 150 may further comprise an angle adjustment mechanism (not shown) for easy lifting of the visor from an in-use position to a stowed position, i.e., not in-use.

In an example, the system may be structured and arranged to redistribute one or more components from the display unit to the positioning and stabilizing structure, e.g., to redistribute weight from the display unit to the positioning and stabilizing structure. For example, the forehead support rigidiser 156 and/or forehead support strap 148 may be used to at least partially support one or more non-location essential electrical components, e.g., batteries, hard drive storage, to shift weight from the front of the user's head to a more central location, i.e., to counterbalance weight of the display unit. In alternative examples, one or more components from the display unit may be at least partially supported by the rear support hoop 116 and/or temporal connectors 118 to redistribute weight.

FIGS. 4A to 4C show a support for a head-mounted display system or assembly 210 according to a third example of the present technology. In FIGS. 4A to 4C, like reference numerals denote similar or like parts to FIGS. 2A to 2C with the addition of 200 to allow distinguishing between examples, e.g., display unit 212, user interface structure 213, positioning and stabilizing structure 214, rear support hoop 216, temporal connector 218, posterior edge region 220, display unit housing 222, temporal arm 226, parietal portion 238, occipital portion 240, connection straps 242. In the third example, the support for a head-mounted display assembly 210 does not comprise a forehead support, i.e., the display unit 212 is supported by a positioning and stabilizing structure 214 without any forehead support connector or forehead support straps.

Figure 5:
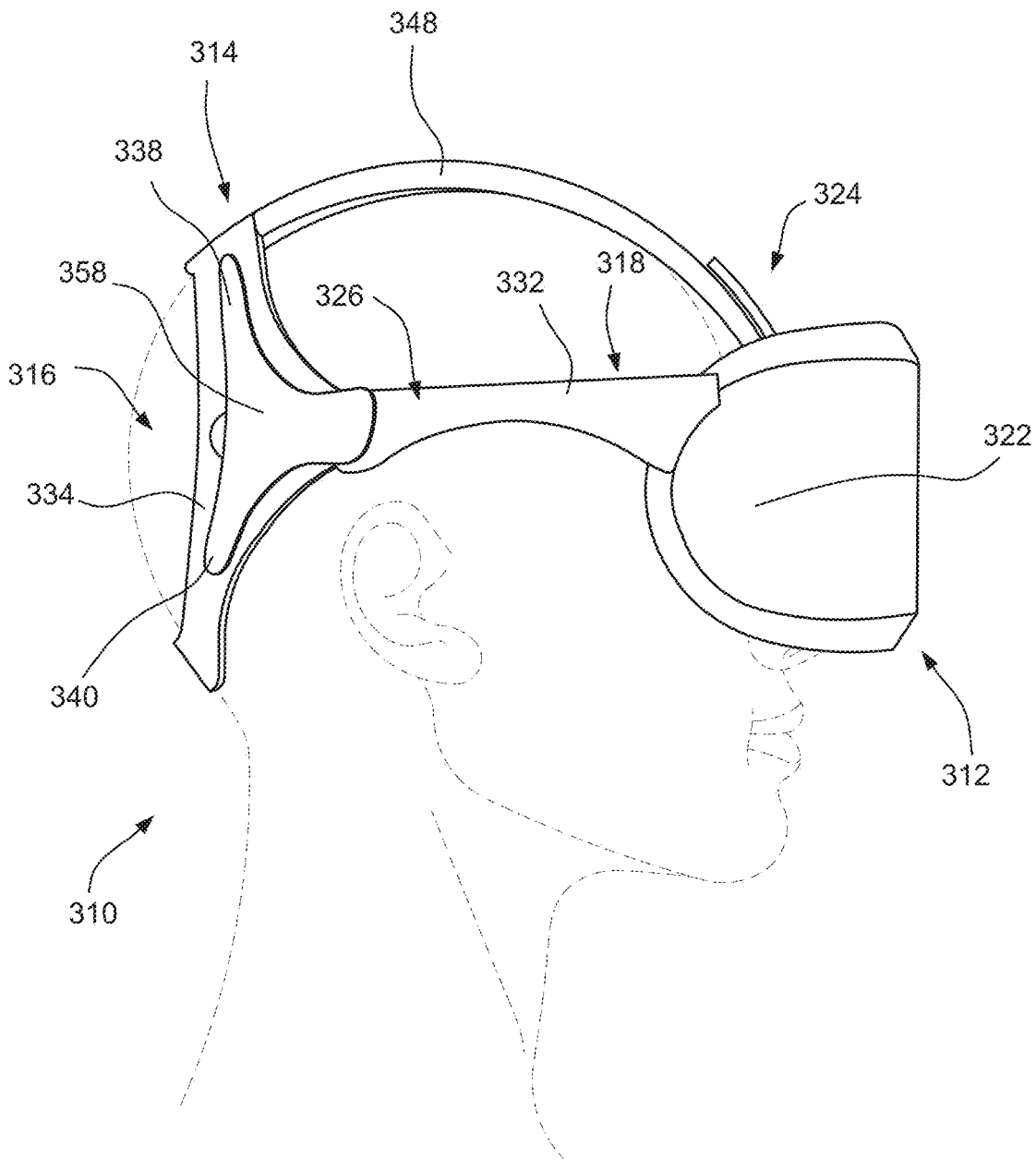
FIG. 5 is a side view of a head-mounted display assembly in-use according to a fourth example of the present technology.

FIG. 5 shows a support for a head-mounted display system or assembly 310 according to a fourth example of the present technology. In FIG. 5, like reference numerals denote similar or like parts to FIGS. 2A to 2C with the addition of 300 to allowing distinguishing between examples, e.g., display unit 312, user interface structure 313, positioning and stabilizing structure 314, rear support hoop 316, temporal connector 318, display unit housing 322, forehead support connector 324, temporal arm 326, rigidiser 332, parietal portion 338, occipital portion 340, forehead support strap 348. In the fourth example, the support for a head-mounted display system 310 comprises opposing temporal connectors 318 each having a temporal arm 326 with an extended rigidiser 358. Each extended rigidiser 358 may extend from the respective temporal arm 326 to the rear support hoop 316 to enhance support of the display unit 312, in use. Each extended rigidiser 358 may extend along a portion of the rear support hoop 316 and may extend into one or both of the parietal portion 338 and the occipital portion 340. For example, each extended rigidiser 358 may comprise a Y-shaped form as shown in FIG. 5 that extends into both the parietal portion 338 and the occipital portion 340. Alternatively, each extended rigidiser 358 may only extend into one of the parietal portion 338 and the occipital portion 340, e.g., only extend along the occipital portion 340 as shown in FIG. 6A discussed below. In the example of FIG. 5, the parietal and occipital portions of the extended arms of the rigidiser 358 are provided along the parietal portion 338 and occipital portion 340 of the rear support hoop 316 positioned proximal to the parietal and occipital bones of the user's head to support respective portions of the rear support hoop 316.

The extended rigidisers 358 increase the length of the temporal connectors 318 so as to increase the lever-arm moment created about the rear support hoop 316. In use, the larger lever-arm extends the moment of inertia further rearward of the user's head when compared the first and second examples. Advantageously, this can provide more comfort to the user by decreasing the tension applied to the forehead support connector 324 to support the display unit 312.

Additionally, the extended arms of the rigidiser 358 may provide a more even distribution of pressure on the user's head under the weight of the display unit 312 and any clamping force applied by tension induced in the positioning and stabilising structure 314.

The extended arms of the rigidiser 358 can help prevent the rear support hoop 316 of the positioning and stabilising structure 314 from translating vertically upwards on the user's head when tensioning the forehead support connector 324. The extended arms of the rigidiser 358 can more effectively secure the occipital portion 340 of the rear support hoop 316 along the corresponding occipital bone (e.g., along a portion of the occipital bone adjacent a junction where the neck muscles attach to the occipital bone) of the user's head.

Figure 6C:
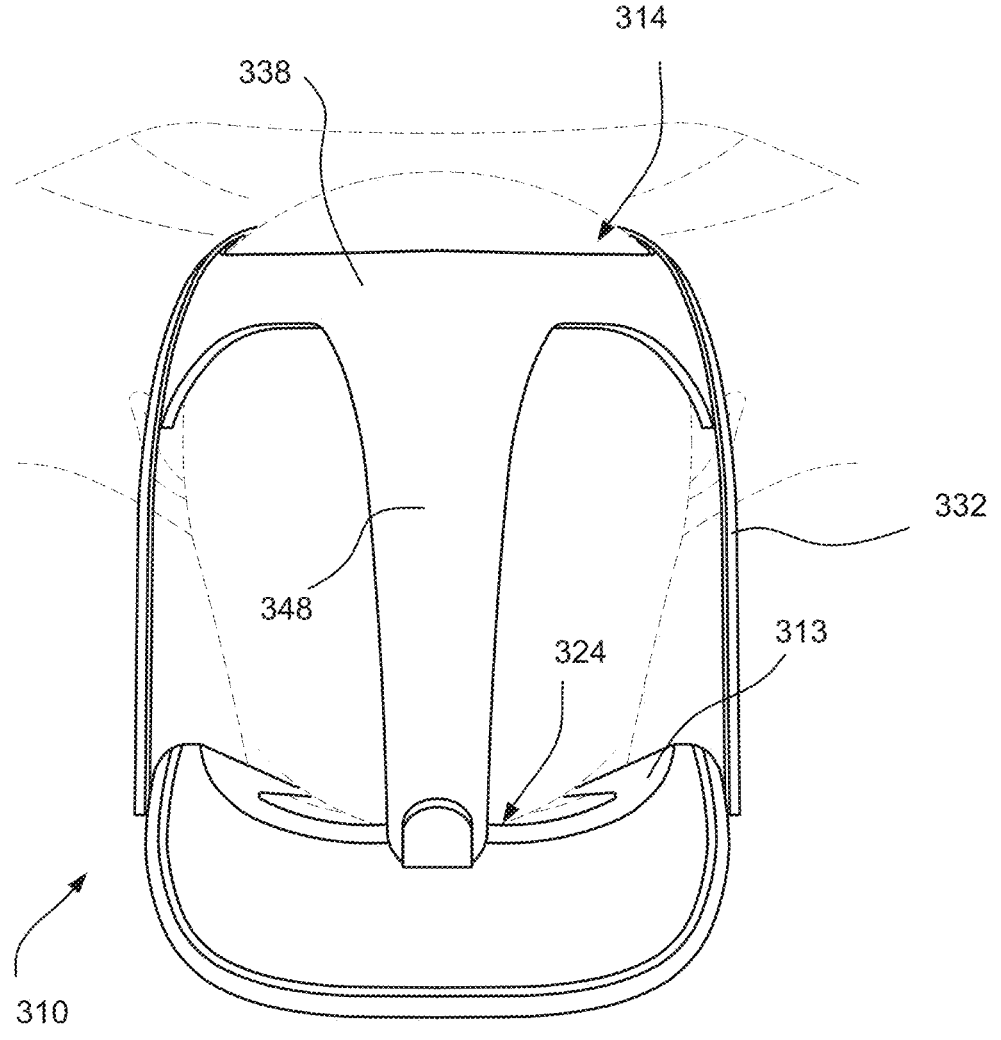

FIGS. 6A to 6C show a variation of the fourth example in FIG. 5. In this example, each of the temporal arms 326 comprises a biased extended rigidiser 360. Each biased extended rigidiser 360 may extend from the respective temporal arm 326 to the occipital portion 340 of the rear support hoop 316, i.e., to generally take a J-shaped form, so as to enhance support of the display unit 312, in use.

The biased extended rigidisers 360 extend along a portion of the occipital bone, e.g., along a portion of the occipital bone adjacent a junction where the neck muscles attach to the occipital bone, to securely anchor the positioning and stabilising structure 314 so as to support the display unit 312 above the user's nose and cheek.

As best shown in FIGS. 6A and 6B, medial and temporal adjustment mechanisms 362, 364 may be provided to the temporal arms 326 and the biased extended rigidisers 360. The medial adjustment mechanism 362 can be mounted about the medial region of the occipital portion between opposed arms of the biased extended rigidisers 360. In an example, the medial adjustment mechanism 362 may be in the form of a strap threaded through opposing holes 363 in respective posterior ends 368 of the opposing arms of the biased extended rigidisers 360 (see FIG. 6B). The distance between the opposing arms of the rigidisers 360 can be controlled by pulling more or less of the strap 362 through the holes 363.

The temporal adjustment mechanism 364 can be disposed on the temporal arm 326, along the temporal region of the user's head. The temporal adjustment mechanism 364 can be adjustable and operate to change the distance between the biased extended rigidisers 360 and the display unit housing 322.

The above-described head-mounted display systems provide alternative examples of the present technology structured and arranged to enhance comfort, fit range, usability, system architecture, use in a medical environment, and manufacturability.

The head-mounted display systems according to examples of the present technology provide enhanced comfort with minimised facial markings and pain from prolonged use. For example, comfort may be achieved by providing universal load distribution in which load is optimised on all contact surfaces by avoiding or minimising load on areas prone to discomfort and redistributing this load to areas able to comfortably bare the load, e.g., avoid or minimise load on the nasal bridge and sides of the nose and apply or redistribute this load to the top and/or rear of the head. Also, comfort may be achieved by providing regional load distribution in which load is evenly distributed by design and material selection in regions of the face where contact is unavoidable, e.g., contact points around the eyes may comprise compliant materials that evenly distribute load and avoid pain points/facial marking. In addition, comfort may be achieved by minimising weight as less weight in the overall system leads to less tension to position and maintain the system in the right configuration. In this regard, the head-mounted display systems according to examples of the present technology provide a minimalist design (e.g., low profile) to achieve fit range, comfort, and correct configuration, e.g., componentry optimised to minimize size and number of components to achieve function and use of robust and lightweight materials.

The head-mounted display systems according to examples of the present technology provide enhanced fit range or universal fit without trading off comfort, usability and cost. For example, fit range may be achieved by providing adjustability with geometry and material selection and adjustment mechanism. The components of the positioning and stabilising structure are designed and materials may be selected to provide desired force versus displacement, e.g., straps may stretch to a desired length under a predetermined force. The adjustment mechanism provides simplicity as sizing of the positioning and stabilising structure and associated straps may be manually adjusted and set, and componentry can be minimised while maximising ease of use, e.g., single handed adjustment of straps and alternative use of magnetic clips for connection. Also, the adjustment mechanism provides minimal size and weight which reduces the bulk of adjustment mechanisms with optimal materials and minimal components. Further, enhanced fit range may be achieved by anthropometrics in which adjustment range may be designed to fit the optimal anthropometric range of the desired market.

The head-mounted display systems according to examples of the present technology provide enhanced usability with low-touch simple set up solutions and low dexterity threshold solutions. For example, low-touch set up may be achieved with self-adjusting solutions including stretchable materials or simple mechanical actuation where only a few minor adjustments may be necessary for correct fit. Also, the system may include adjust and lock solutions to facilitate usability (i.e., set and forget), e.g., mechanisms to guide adjustment (e.g., magnets) and locking mechanisms to set adjustment (e.g., clips). Further, the system provides ease of use so that it is capable of adjustment when worn by a user with low-dexterity and/or minimal vision.

The head-mounted display systems according to examples of the present technology provide enhanced system architecture which optimises componentry location such that it minimises cost while maximising comfort, fit range and usability. For example, the system may provide enhanced weight distribution in which electrical and/or mechanical components are positioned in ideal locations from a comfort perspective. Also, the system may comprise modularity such that components may be selected or upgraded based on user preference, e.g., electrical component, face contacting cushions, straps, and/or ear buds may be selected based on preference.

The head-mounted display systems according to examples of the present technology enhance use in a medical environment. For example, the system may be biocompatible and/or cleanable with materials selected that are cleanable for re-use in a medical environment and/or pass biocompatibility requirements.

The head-mounted display systems according to examples of the present technology enhance manufacturability by providing mass producible solutions at low cost while maintaining high quality and functionality.

In the claims which follow and in the preceding description of examples of the present technology, except where the context requires otherwise due to express language or necessary implication, the word "comprise" or variations such as "comprises" or "comprising" is used in an inclusive sense, i.e., to specify the presence of the stated features but not to preclude the presence or addition of further features in various examples of the present technology.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements or examples. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST

| Feature Item | Number |
| --- | --- |
| head-mounted display system | 10 |
| display unit | 12 |
| user interface structure | 13 |
| positioning and stabilising structure | 14 |
| rear support hoop | 16 |
| temporal connectors | 18 |
| posterior edge region | 20 |
| superior edge region | 21 |
| display unit housing | 22 |
| forehead support connector | 24 |
| temporal arm | 26 |
| anterior end | 28 |
| posterior end | 30 |
| rigidiser | 32 |
| textile component | 34 |
| face contacting surface | 35 |
| tab | 36 |
| parietal portion | 38 |
| occipital portion | 40 |
| connection straps | 42 |
| eyelet | 44 |
| forehead support strap | 48 |
| adjustment mechanism | 50 |
| forehead support hole | 52 |
| tab portion | 54 |
| head-mounted display system | 110 |
| display unit | 112 |
| user interface structure | 113 |
| positioning and stabilising structure | 114 |
| rear support hoop | 116 |
| temporal connector | 118 |
| posterior edge region | 120 |
| superior edge region | 121 |
| display unit housing | 122 |
| forehead support connector | 124 |
| temporal arm | 126 |
| parietal portion | 138 |
| occipital portion | 140 |
| connection straps | 142 |
| forehead support strap | 148 |
| adjustment mechanism | 150 |
| forehead support hole | 152 |
| tab portion | 154 |
| forehead support rigidiser | 156 |
| head-mounted display system | 210 |
| display unit | 212 |
| user interface structure | 213 |
| positioning and stabilising structure | 214 |
| rear support hoop | 216 |
| temporal connector | 218 |
| posterior edge region | 220 |
| display unit housing | 222 |
| temporal arm | 226 |
| parietal portion | 238 |
| occipital portion | 240 |
| connection straps | 242 |
| head-mounted display system | 310 |
| display unit | 312 |
| user interface structure | 313 |
| positioning and stabilising structure | 314 |
| rear support hoop | 316 |
| temporal connectors | 318 |
| temporal connector | 318 |
| display unit housing | 322 |
| forehead support connector | 324 |
| temporal arm | 326 |

-continued

REFERENCE SIGNS LIST

| Feature Item | Number |
| --- | --- |
| rigidiser | 332 |
| parietal portion | 338 |
| occipital portion | 340 |
| forehead support strap | 348 |
| extended rigidiser | 358 |
| biased extended rigidiser | 360 |
| medial adjustment mechanism | 362 |
| holes | 363 |
| temporal adjustment mechanism | 364 |
| posterior ends | 368 |

The invention claimed is:

1. A positioning and stabilising structure configured to hold a head-mounted display unit in an operational position in front of a user's eyes in use, the positioning and stabilising structure comprising:

a rear support structure configured to contact posterior regions of a user's head, wherein the rear support structure comprises an occipital portion configured to engage the user's head along a portion of the occipital bone and a parietal portion configured to overlay the parietal bones of the user's head in use;

an adjustment mechanism provided to the occipital portion of the rear support structure, the adjustment mechanism configured to adjust a length of the occipital portion to fit different size heads; and a pair of lateral portions, each of the pair of lateral portions configured to be positioned on a respective lateral side of the user's head in use, wherein the pair of lateral portions are disposed between the occipital portion and the parietal portion, and wherein each of the lateral portions comprises a connector configured to connect to a respective one of a pair of temporal arms extending posteriorly from the display unit.

2. The positioning and stabilising structure of claim 1, wherein the positioning and stabilising structure is configured to counterbalance weight from the display unit.

3. The positioning and stabilising structure of claim 1, wherein the positioning and stabilising structure is configured to support one or more components to shift weight from a front of the user's head to a more central location.

4. The positioning and stabilising structure of claim 1, wherein the rear support structure has a three-dimensional shape in the form of a hoop prior to contacting the user's head.

5. The positioning and stabilising structure of claim 4, wherein the hoop is resiliently extensible along at least a portion of its length.

6. The positioning and stabilizing structure of claim 1, wherein the rear support structure and/or the pair of lateral portions comprises a textile material configured to conform to the user's head.

7. The positioning and stabilizing structure of claim 6, wherein the textile material is an outer layer, and wherein the rear support structure and/or the pair of lateral portions further comprises an inner foam layer surrounded by the textile material.

8. The positioning and stabilizing structure of claim 1, wherein the rear support structure and/or the pair of lateral portions comprises a textile-foam composite configured to conform to the user's head.

9. The positioning and stabilizing structure of claim 1, wherein each of the pair of temporal arms is rigid along its entire length.

10. The positioning and stabilizing structure of claim 1, wherein the rear support structure and/or the pair of lateral portions are at least partially formed from an elastic material.

11. The positioning and stabilising structure of claim 1, wherein each of the pair of temporal arms includes an anterior end connected to the head-mounted display unit and a posterior end connected to a respective connector.

12. The positioning and stabilizing structure of claim 1, wherein the adjustment mechanism comprises a strap threaded through a hole.

13. A head-mounted display system, comprising:
a display unit; and
the positioning and stabilising structure of claim 1.

14. The head-mounted display system of claim 13, wherein the display unit comprises a display unit housing including a display configured to be visible to the user when the display unit is in the operational position.

\* \* \* \* \*